US006627234B1

(12) United States Patent
Johnson et al.

(10) Patent No.: US 6,627,234 B1
(45) Date of Patent: Sep. 30, 2003

(54) METHOD OF PRODUCING ACTIVE AGENT COATED CHEWING GUM PRODUCTS

(75) Inventors: Sonya S. Johnson, LaGrange Highlands, IL (US); David W. Record, River Forest, IL (US); Michael J. Greenberg, Northbrook, IL (US); Michael A. Reed, Merrillville, IN (US); Victor V. Gudas, Oak Lawn, IL (US); Philip G. Schnell, Downers Grove, IL (US); Donald A. Seielstad, Frankfurt, IL (US); Henry T. Tyrpin, Palos Park, IL (US); Michael P. Russell, Evergreen Park, IL (US); David L. Witkewitz, Bridgeview, IL (US); Joo H. Song, Chicago, IL (US); Donald J. Townsend, Moores Hill, IN (US); Robert J. Yatka, Orland Park, IL (US); Ronald L. Ream, Plano, IL (US); Christine L. Corriveau, Orland Park, IL (US); William J. Wokas, Bolingbrook, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/621,643

(22) Filed: Jul. 21, 2000

Related U.S. Application Data

(63) Continuation of application No. PCT/US99/29742, filed on Dec. 14, 1999, which is a continuation-in-part of application No. 09/389,211, filed on Sep. 2, 1999, now abandoned, and a continuation-in-part of application No. 09/308,972, filed as application No. PCT/US96/18977 on Nov. 27, 1996, now Pat. No. 6,165,516, and a continuation-in-part of application No. 09/286,818, filed on Apr. 6, 1999.

(51) Int. Cl.[7] ............................. A23G 3/30; A61K 9/68
(52) U.S. Cl. ..................... 426/5; 424/48; 424/440
(58) Field of Search ........................... 426/3, 5; 424/48, 424/440

(56) References Cited

U.S. PATENT DOCUMENTS

| | | |
|---|---|---|
| 1,298,670 A | 4/1919 | Cramer |
| 1,629,461 A | 5/1927 | Berg et al. |
| 2,892,753 A | 6/1959 | Ludwig Schmidt et al. |
| 2,990,328 A | 6/1961 | Lincoln |
| 3,011,949 A | 12/1961 | Bilotti |
| 3,029,189 A | 4/1962 | Hardy et al. |
| 3,047,461 A | 7/1962 | Hardy et al. |
| 3,075,884 A | 1/1963 | Bilotti et al. |
| 3,196,172 A | 7/1965 | Wright, Jr. et al. |
| 3,308,022 A | 3/1967 | Cummings et al. |
| 3,498,964 A | 3/1970 | Hayashi |
| 3,554,767 A | 1/1971 | Daum |
| 3,590,057 A | 6/1971 | Suzuki et al. |
| 3,845,217 A | 10/1974 | Ferno et al. ............. 426/3 |
| 3,877,468 A | 4/1975 | Lichtneckert et al. ...... 131/2 |
| 3,901,248 A | 8/1975 | Lichtneckert et al. ...... 131/2 |
| 3,995,064 A | 11/1976 | Ehrgott et al. ............. 426/3 |
| 4,154,814 A | 5/1979 | Hand et al. |
| 4,238,475 A | 12/1980 | Witzel et al. ............. 424/48 |
| 4,238,510 A | 12/1980 | Cherukuri et al. .......... 426/5 |
| 4,250,195 A | 2/1981 | Cherukuri et al. |
| 4,283,408 A | 8/1981 | Hirata et al. ............. 424/270 |
| 4,317,838 A | 3/1982 | Cherukuri et al. .......... 426/5 |
| 4,374,858 A | 2/1983 | Glass et al. |
| 4,378,374 A | 3/1983 | Reggio et al. |
| 4,386,063 A | 5/1983 | Boden |
| 4,386,106 A | 5/1983 | Merrit et al. |
| 4,400,372 A | 8/1983 | Munker et al. |
| 4,446,135 A | 5/1984 | Fountaine ............. 424/154 |
| 4,452,821 A | 6/1984 | Gergely ............... 426/5 |
| 4,459,311 A | 7/1984 | DeTora et al. .......... 426/3 |
| 4,474,749 A | 10/1984 | Kruppa |
| 4,512,968 A | 4/1985 | Komiyama et al. ........ 424/48 |
| 4,533,556 A | 8/1985 | Piccolo et al. |
| 4,555,407 A | 11/1985 | Kramer et al. .......... 426/5 |
| 4,563,345 A | 1/1986 | Arrick |
| 4,639,368 A | 1/1987 | Niazi et al. ............ 424/48 |
| 4,647,450 A | 3/1987 | Peters et al. |
| 4,711,774 A | 12/1987 | Denick, Jr. et al. ....... 424/48 |
| 4,716,033 A | 12/1987 | Denick, Jr. .............. 424/48 |
| 4,737,366 A | 4/1988 | Gergely et al. .......... 426/5 |
| 4,753,800 A | 6/1988 | Mozda |
| 4,753,805 A | 6/1988 | Cherukuri et al. ......... 426/5 |
| 4,755,389 A | 7/1988 | Jones et al. |
| 4,758,424 A | 7/1988 | Denick, Jr. et al. ....... 424/48 |
| 4,822,597 A | 4/1989 | Faust et al. |
| 4,822,816 A | 4/1989 | Markham |

(List continued on next page.)

FOREIGN PATENT DOCUMENTS

| | | |
|---|---|---|
| DE | 43 42 568 A1 | 6/1994 |
| EP | 0 202 819 A2 | 11/1986 |
| EP | 0 217 109 A2 | 4/1987 |
| EP | 0 221 850 | 5/1987 |
| EP | 0 239 541 A2 | 9/1987 |

(List continued on next page.)

OTHER PUBLICATIONS

"Flavor Encapsulation Technologies, Flavor Unit Sweet, Product Management", H&R (undated) (published at least before Nov. 27, 1996), 25 pages.

(List continued on next page.)

Primary Examiner—Arthur L. Corbin
(74) Attorney, Agent, or Firm—Steven P. Shurtz; Brinks Hofer Gilson & Lione

(57) ABSTRACT

A method for producing a chewing gum with an improved release of active agent, as well as the chewing gum so produced, is obtained by adding an active agent to a chewing gum coating. The active agent is added to the coating in a coating solution or premixed with a flavor or solvent. The coating solution may contain sweetener or other transdermal enhancing agents to obtain increased transmucosal absorption. An active agent may also be used in the gum core.

14 Claims, No Drawings

U.S. PATENT DOCUMENTS

| | | | |
|---|---|---|---|
| 4,828,820 A | 5/1989 | Glass et al. | |
| 4,832,994 A | 5/1989 | Fey | |
| 4,835,162 A | 5/1989 | Abood | 514/305 |
| 4,849,227 A | 7/1989 | Cho | |
| 4,853,212 A | 8/1989 | Faust et al. | |
| 4,867,989 A | 9/1989 | Silva et al. | 426/5 |
| 4,882,152 A | 11/1989 | Yang et al. | 424/440 |
| 4,894,234 A | 1/1990 | Sharma et al. | 424/440 |
| 4,908,211 A | 3/1990 | Paz | |
| 4,908,212 A | 3/1990 | Kwon et al. | |
| 4,929,447 A | 5/1990 | Yang | |
| 4,929,508 A | 5/1990 | Sharma et al. | 424/439 |
| 4,933,184 A | 6/1990 | Tsuk | |
| 4,935,242 A | 6/1990 | Sharma et al. | 424/439 |
| 4,938,963 A | 7/1990 | Parnell | |
| 4,944,949 A | 7/1990 | Story et al. | |
| 4,963,369 A | 10/1990 | Song et al. | 426/5 |
| 4,968,511 A | 11/1990 | D'Amelia et al. | 426/6 |
| 4,968,716 A | 11/1990 | Markham | |
| 4,971,079 A | 11/1990 | Talapin et al. | 131/359 |
| 4,971,787 A | 11/1990 | Cherukuri et al. | 414/48 |
| 4,975,270 A | 12/1990 | Kehoe | 424/48 |
| 4,978,537 A | 12/1990 | Song | 426/5 |
| 4,997,659 A | 3/1991 | Yatka et al. | 426/3 |
| 5,013,716 A | 5/1991 | Cherukuri et al. | 514/23 |
| 5,015,464 A | 5/1991 | Strobridge | |
| 5,045,325 A | 9/1991 | Lesko et al. | 426/5 |
| 5,070,085 A | 12/1991 | Markham | |
| 5,110,608 A | 5/1992 | Cherukuri | |
| 5,124,156 A | 6/1992 | Shibata et al. | |
| 5,126,151 A | 6/1992 | Bodor et al. | |
| 5,139,787 A | 8/1992 | Broderick et al. | |
| 5,139,794 A | 8/1992 | Patel et al. | 426/3 |
| 5,154,927 A | 10/1992 | Song et al. | |
| 5,156,842 A | 10/1992 | Mulligan | |
| 5,179,122 A | 1/1993 | Greene et al. | |
| 5,182,099 A | 1/1993 | Jonsson et al. | |
| 5,229,137 A | 7/1993 | Wolfe | 424/687 |
| 5,244,670 A | 9/1993 | Upson et al. | 424/439 |
| 5,284,657 A | 2/1994 | Lu et al. | |
| 5,286,500 A | 2/1994 | Synosky et al. | 426/3 |
| 5,294,433 A | 3/1994 | Singer et al. | |
| 5,294,449 A | 3/1994 | Greenberg | |
| 5,340,566 A | 8/1994 | Curtis et al. | |
| 5,378,131 A | 1/1995 | Greenberg | |
| 5,380,530 A | 1/1995 | Hill | |
| 5,380,535 A | 1/1995 | Geyer et al. | |
| 5,397,580 A | 3/1995 | Song et al. | 426/5 |
| 5,410,028 A | 4/1995 | Asami et al. | |
| 5,419,919 A | 5/1995 | Song et al. | 426/5 |
| 5,433,960 A | 7/1995 | Meyers | 426/5 |
| 5,445,834 A | 8/1995 | Burger et al. | |
| 5,455,286 A | 10/1995 | Amidon et al. | |
| 5,456,677 A | 10/1995 | Spector | 604/290 |
| 5,487,902 A | 1/1996 | Andersen et al. | 426/3 |
| 5,488,962 A | 2/1996 | Perfetti | |
| 5,494,685 A | 2/1996 | Tyrpin et al. | 426/5 |
| 5,496,541 A | 3/1996 | Cutler | |
| 5,512,306 A | 4/1996 | Carlsson et al. | |
| 5,523,097 A | 6/1996 | Song et al. | 426/3 |
| 5,534,272 A | 7/1996 | Bernstein | |
| 5,536,511 A | 7/1996 | Yatka | 426/5 |
| 5,543,160 A | 8/1996 | Song et al. | 426/3 |
| 5,554,380 A | 9/1996 | Cuca et al. | |
| 5,569,477 A | 10/1996 | Nesbitt | 426/5 |
| 5,571,528 A | 11/1996 | Lee et al. | |
| 5,571,543 A | 11/1996 | Song et al. | 426/5 |
| 5,576,344 A | 11/1996 | Sandler et al. | 514/429 |
| 5,580,590 A | 12/1996 | Hartman | 426/3 |
| 5,582,855 A | 12/1996 | Cherukuri et al. | 426/5 |
| 5,585,110 A | 12/1996 | Kalili et al. | |
| 5,593,685 A | 1/1997 | Bye et al. | |
| 5,601,858 A | 2/1997 | Manshukhani et al. | |
| 5,605,698 A | 2/1997 | Ueno | |
| 5,607,697 A | 3/1997 | Alkire et al. | 424/495 |
| 5,618,517 A | 4/1997 | Miskewitz | |
| 5,628,986 A | 5/1997 | Sanker et al. | |
| 5,629,013 A | 5/1997 | Upson et al. | 424/441 |
| 5,629,026 A | 5/1997 | Davis | 424/686 |
| 5,629,035 A | 5/1997 | Miskewitz | |
| 5,645,853 A | 7/1997 | Winston et al. | |
| 5,651,987 A | 7/1997 | Fuysz | 424/488 |
| 5,656,652 A | 8/1997 | Davis | 514/400 |
| 5,665,386 A | 9/1997 | Bebet et al. | |
| 5,665,406 A | 9/1997 | Reed et al. | 426/5 |
| 5,667,802 A | 9/1997 | Grimberg | |
| 5,693,334 A | 12/1997 | Miskewitz | |
| 5,698,215 A | 12/1997 | Kalili et al. | |
| 5,702,687 A | 12/1997 | Miskewitz | |
| 5,711,961 A | 1/1998 | Reiner et al. | 424/441 |
| 5,716,928 A | 2/1998 | Benet et al. | |
| 5,736,175 A | 4/1998 | Cea et al. | |
| 5,744,164 A | 4/1998 | Chauffard et al. | |
| 5,753,255 A | 5/1998 | Chavkin et al. | |
| 5,756,074 A | 5/1998 | Ascione et al. | |
| 5,800,847 A | 9/1998 | Song et al. | 426/3 |
| 5,824,291 A | 10/1998 | Howard | |
| 5,834,002 A | 11/1998 | Athanikar | 424/440 |
| 5,846,557 A | 12/1998 | Eisenstadt et al. | 424/439 |
| 5,854,267 A | 12/1998 | Berlin et al. | 514/370 |
| 5,858,383 A | 1/1999 | Precopio | 424/405 |
| 5,858,412 A | 1/1999 | Staniforth et al. | 424/489 |
| 5,858,413 A | 1/1999 | Jettka et al. | 424/682 |
| 5,858,423 A | 1/1999 | Vajima et al. | 426/3 |
| 5,866,179 A | 2/1999 | Testa | 426/3 |
| 5,877,173 A | 3/1999 | Olney et al. | 514/217 |
| 5,882,702 A | 3/1999 | Abdel-Malik et al. | |
| 5,889,028 A | 3/1999 | Sandborn et al. | 514/343 |
| 5,889,029 A | 3/1999 | Rolf | 514/343 |
| 5,897,891 A | 4/1999 | Godfrey | 426/74 |
| 5,900,230 A | 5/1999 | Cutler | |
| 5,912,007 A | 6/1999 | Pan et al. | 424/440 |
| 5,912,030 A | 6/1999 | Huzoinec et al. | |
| 5,916,606 A | 6/1999 | Record et al. | 426/3 |
| 5,922,346 A | 7/1999 | Hersh | |
| 5,922,347 A | 7/1999 | Häusler et al. | 424/441 |
| 5,928,664 A | 7/1999 | Yang et al. | 424/440 |
| 5,958,380 A | 9/1999 | Winston et al. | |
| 5,958,472 A | 9/1999 | Robinson et al. | |
| 5,980,955 A | 11/1999 | Greenberg et al. | 426/5 |
| 5,989,588 A | 11/1999 | Korn et al. | 424/465 |
| 6,024,988 A | 2/2000 | Ream et al. | 426/3 |
| 6,066,342 A | 5/2000 | Gurol et al. | 424/687 |
| 6,077,524 A | 6/2000 | Bolder et al. | |
| 6,090,412 A | 7/2000 | Hashimoto et al. | 424/490 |
| 6,165,516 A | 12/2000 | Gudas et al. | |
| 6,221,402 B1 | 2/2001 | Itoh et al. | 424/494 |
| 6,200,604 B1 | 3/2001 | Pather et al. | 424/466 |
| 6,258,376 B1 | 7/2001 | Athanikar | 424/440 |
| 6,290,985 B2 | 9/2001 | Ream et al. | 424/440 |
| 6,303,159 B2 | 10/2001 | Barkalow et al. | 426/5 |
| 6,322,806 B1 | 11/2001 | Ream et al. | 424/440 |
| 6,350,480 B1 | 2/2002 | Urnezis et al. | 426/5 |
| 6,355,265 B1 | 3/2002 | Ream et al. | 424/440 |
| 2001/0036445 A1 | 11/2001 | Anthanikar | 424/48 |
| 2002/0012633 A1 | 1/2002 | Gmunder et al. | 424/48 |
| 2002/0022057 A1 | 2/2002 | Battey et al. | 424/490 |

FOREIGN PATENT DOCUMENTS

| | | |
|---|---|---|
| EP | 0 273 809 B1 | 12/1987 |
| EP | 0 371 584 A2 | 6/1990 |

| | | |
|---|---|---|
| FR | 2 345 938 | 10/1977 |
| FR | 2 635 441 | 2/1990 |
| FR | 2 706 771 | 6/1993 |
| GB | 0 934 596 | 8/1963 |
| GB | 0 963 518 | 7/1964 |
| GB | 1 489 832 | 10/1977 |
| GB | 2 181 646 A | 4/1987 |
| IT | 01273487 | 7/1997 |
| IT | 01293655 | 3/1999 |
| JP | 86-242561 | 10/1986 |
| JP | 91-112450 | 5/1991 |
| JP | 91-251533 | 11/1991 |
| JP | 94-303911 | 11/1994 |
| JP | 96-19370 | 1/1996 |
| KR | 94-2868 | 4/1994 |
| WO | WO 84/02271 | 6/1984 |
| WO | WO 90/12511 | 11/1990 |
| WO | WO 90/12583 | 11/1990 |
| WO | WO 92/06680 | 4/1992 |
| WO | WO 95/00038 | 1/1995 |
| WO | WO 95/00039 | 1/1995 |
| WO | WO 95/10290 | 4/1995 |
| WO | WO 96/00070 | 1/1996 |
| WO | WO 96/03975 | 2/1996 |
| WO | WO 97/21424 | 6/1997 |
| WO | WO 97/24036 | 6/1997 |
| WO | WO 98/23165 | 6/1998 |
| WO | WO 98/23166 | 6/1998 |
| WO | WO 98/23167 | 6/1998 |
| WO | WO 99/27798 | 6/1999 |
| WO | WO 99/33352 | 7/1999 |
| WO | WO 99/44436 | 9/1999 |
| WO | WO 00/13523 | 3/2000 |
| WO | WO 00/35296 | 6/2000 |
| WO | WO 00/35298 | 6/2000 |
| WO | WO 00/38532 | 7/2000 |
| WO | WO 02/13781 A1 | 2/2002 |

OTHER PUBLICATIONS

Dr. Massimo Calanchi and Dr. Sam Ghanta, "Taste–masking of oral formulations", *Eurand International SpA, Pharmaceutical Manufacturing International,* 1996 (5 pages).

The Eurand Group, Brochure (undated) (published at least before Nov. 27, 1996), (16 pages).

Merck Index, 11$^{th}$ Ed., #1635 "Caffeine" (1989), p. 248.

Merck Index, 12$^{th}$ Ed., #2337 "Cimetidine" (1996), p. 383.

Merck Index, 12$^{th}$ Ed., #3264 "Dimethicone" (1996), p. 544.

Merck Index, 12$^{th}$ Ed., #3972 "Famotidine" (1996), p. 667.

Merck Index, 12$^{th}$ Ed., #6758 "Nizatidine" (1996), p. 1143.

Merck Index, 12$^{th}$ Ed., #6977 "Omeprazole" (1996), p. 1174.

Merck Index, 12$^{th}$ Ed., #8272 "Rabeprazole" (1996), p. 1392.

Merck Index, 12$^{th}$ Ed., #8286 "Ranitidine" (1996), p. 1395.

James G. Elliott, "Aplication of Antioxidant Vitamins in Foods and Beverages" *Food Technology,* (Feb., 1999), pp. 46–48.

C. Curtis Vreeland, "Nutraceuticals Fuel Confectionery Growth" *Candy R&D,* (Mar., 1999), pp. 29, 31–32, 34–35.

Kitty Broihier, R.D., "Foods of Tomorrow, Milking The Nutrition Market", *Food Processing,* (Mar. 1999), pp. 41, 42 and 44.

Kitty Broihier, R.D., "Tea Time For Nutraceuticals, New Black, Green Tea Products Brew Up a Bevy of Health Benefits", *Food Processing;* (Mar., 1999), pp. 59, 61 and 63.

Andrea Allen, Jack Neff, Lori Dahm and Mary Ellen Kuhn, "Exclusive Guide to Wellness Foods and Nutraceuticals", Food Processing (Special Supplement), Mar., 1999).

Product package "Aspergum" distributed by Heritage Consumer Products, LLC (on sale prior to Nov. 27, 1995).

Product package "Chem & Sooth Zinc Dietary Supplement Gum" by Gumtech International, Inc. (undated).

Product package "Dental Care the Baking Soda Gum" distributed by Church & Dwight Co., Inc. (1998).

Product package "BreatAsure Dental Gum" distributed by Breath Asure, Inc. (1998).

Product package "Trident Advantage with Baking Soda" distributed by Warner–Lambert Co. (1998).

Product package "CHOOZ Antacid/Calcium Supplement with Calcium Carbonate" distributed by Heritage Consumer Products Co.

Hertiage Consumer Products Co. article from the Internet "Cosmetics and Toiletries, The Heritage Story", printed Jul. 20, 2000, <http://www.cnewsusa.com/Connecticut/14997.html>, 1 page.

The United States Pharmacopeia The National Formulary— "General Information", dated Jan. 1, 1990 pp. 1624–1625 and pp. 1696–1697.

Gumtech article from the Internet "Customized Solutions For Customer Brands", printed Oct. 18, 2000, <http://www.gum–tech.com/cus–brands.html>, 3 pages.

Rabeprazole article from the Internet "Rabeprazole: Pharmacokinetics and Safety in the Elderly", printed Sep. 22, 2000, <http://www.mmhc.com/cg/articles/CG9905/Hum–phries.html>, 2 pages.

Product package for Stay Alert Caffeine Supplement Gum, distributed by Amurol Confections Company (first quarter 1998).

Beckett, A. H. et al., "Buccal absorption of basis drugs and its applicaiton as an in vivo model of passive drug transfer through lipid membranes", *J. Pharm. Pharmac., 19 Suppl,* 1967, pp. 31S–41S.

David S. Weinberg et al. "Sublingual absorption of selected opioid analgesics", *Clin. Pharmacol Ther.,* 1998, vol. 44, pp. 335–342.

Brochure for "Minerals Technologies Specialty Minerals", 1998, 19 pages.

Akitoshi et al., Abstract "Acceleration of Transdermal Absorption of Pharmaceuticals by Essential Oils and Organic Solvents," Chem. Abst., 112:126228t, 1990.

Bradford, A Rapid and Sensitive Method for the Quantification of Microgram Quantities of Protein Utilizing the Principle of Protein–Dye Binding, Analytical Biochemistry, 72:248–254 (1976).

Nielsen et al., P–Glycoprotein as Multidrug Transporter: A Critical Review of Current Multidrug Resistant Cell Lines, Chimica et Biophysica Acta., 1139:169–183 (1992).

Adams, M.W., d–Alpha Tocopheryl Polyethylene glycol 1000 Succinate (Eastman vitamin E TPGS) as an Emulsifier and Bioenhancer for Drugs and Lipophilic Compounds, 6th International Conference on Pharmaceutical Technology, Paris, Jun. 2–4, 1992.

Chang, Tammy et al., "The Effect of Water–Soluble Vitamin E on Cyclosporine Pharmacokinetics in Healthy Volunteers," Abstract in American Society to Clinical Pharmacology and Therapeutics, 57(2):163, Feb. 1995.

Hebert, Mary F. et al.; "Bioavailability of Cyclosporine with Concomitant Rifampin Administration is Markedly Less Than Predicted by Hepatic Enzyme Induction" (1992) *Clin. Pharmacol. Ther.* 52:453–457.

Kronbach, Thomas et al.; "Oxidation of Midazolam and Triazolam by Human Liver Cytochrome P450IIIA4" (1989) *Molec. Pharm.* 36:89–96.

Lalka et al.; "The Hepatic First–Pass Metabolism of Problematic Drugs" (1993) *J. Clin. Pharmacol.* 33:657–669.

Lum et al.; "Clinical Trials of Modulation of Multidrug Resistance. Pharmacokinetic and Pharmacodynamic Considerations" (1993) *Cancer* 72:3502–3514.

Muranishi, Shozo; "Absorption Enhancers" (1990) *Crit. Rev. Ther. Drug Carrier Sys.*, 7:1–33.

Somberg et al.; "The Clinical Implications of First–Pass Metabolism: Treatment Strategies for the 1990's" (1993) *J. Clin. Pharmaocl.* 33:670–673.

Tam, Yun K.; "Individual Variation in First–Pass Metabolism" (1993) *Clin. Pharmacokinet.* 25:300–328.

Van Hoogdalem et al.; "Intestinal Drug Absorption Enhancement: An Overview" (1989) *Pharmacol. Ther.* 44:407–443.

Warren et al.; "Increased Accumulation of Drugs in Multidrug–Resistant Cell Induced by Liposomes" (1992) *Cance Research* 52:3241–3245.

Watkins, Paul B.; "The Role of Cytochromes P–450 in Cyclosporine Metabolism" (1990) *J. Am. Acad. Dermacol.* 23:1301–1309.

Wrighton et al.; "In Vitro Methods for Assessing Human Hepatic Drug Metabolism: Their Use in Drug Development" (1993) 25:453–484.

Wu et al.; "Use of IV and Oral Drug Levels from Cyclosporene (CsA) with Concomitant Rifampin to Differentiate Gut Absorption and Metabolism" (1993) *Pharm. Res.* 10:abstract ppdm8185.

Zamora et al.; "Physical–Chemical Properties Shared by Compounds that Modulate Multidrug Resistance in Human Loukemic Cells" (1988) *Molec. Pharmacol.* 33:454–462.

U.S. patent application Ser. No. 09/681,935, filed Jun. 28, 2001.

U.S. patent application Ser. No. 09/924,914, filed Aug. 8, 2001.

U.S. patent application Ser. No. 09/955,870, filed Sep. 19, 2001.

U.S. patent application Ser. No. 09/956,445, filed Sep. 19, 2001.

U.S. patent application Ser. No. 09/990,628, filed Nov. 13, 2001.

U.S. patent application Ser. No. 09/992,122, filed Nov. 13, 2001.

U.S. patent application Ser. No. 10/024,631, filed Dec. 17, 2001.

U.S. patent application Ser. No. 10/044,113, filed Jan. 9, 2002.

U.S. patent application Ser. No. 09/286,818, filed Apr. 6, 1999.

U.S. patent application Ser. No. 09/421,905, filed Oct. 20, 1999.

U.S. patent application Ser. No. 09/510,878, filed Feb. 23, 2000.

U.S. patent application Ser. No. 09/535,458, filed Mar. 24, 2000.

U.S. patent application Ser. No. 09/552,290, filed Apr. 19, 2000.

U.S. patent application Ser. No. 09/591,256, filed Jun. 9, 2000.

U.S. patent application Ser. No. 09/592,400, filed Jun. 13, 2000.

U.S. patent application Ser. No. 09/618,808, filed Jul. 18, 2000.

U.S. patent application Ser. No. 09/621/780, filed Jul. 21, 2000.

U.S. patent application Ser. No. 09/631,326, filed Aug. 3, 2000.

U.S. patent application Ser. No. 09/651,514, filed Aug. 30, 2000.

U.S. patent application Ser. No. 09/654,464, filed Sep. 1, 2000.

U.S. patent application Ser. No. 09/653,669, filed Sep. 1, 2000.

U.S. patent application Ser. No. 09/671,552, filed Sep. 27, 2000.

U.S. patent application Ser. No. 09/714,571, filed Nov. 16, 2000.

U.S. patent application Ser. No. 09/748,699, filed Dec. 22, 2000.

U.S. patent application Ser. No. 09/747,323, filed Dec. 22, 2000.

U.S. patent application Ser. No. 09/747,300, filed Dec. 22, 2000.

U.S. patent application Ser. No. 09/749,983, filed Dec. 27, 2000.

U.S. patent application Ser. No. 09/759,561, filed Jan. 11, 2001.

METHOD OF PRODUCING ACTIVE AGENT COATED CHEWING GUM PRODUCTS

REFERENCE TO EARLIER FILED APPLICATIONS

The present application claims the benefit under 35 U.S.C. §119(e) of the filing date of U.S. Provisional Patent Application No. 60/112,389, filed Dec. 15, 1998. The present application is a continuation of PCT Application Serial No. PCT/US99/29742, filed Dec. 14, 1999, which designated the United States. Said PCT application is a continuation-in-part of U.S. patent application Ser. No. 09/389,211, filed Sep. 2, 1999, now abandoned, a continuation-in-part of U.S. patent application Ser. No. 09/286,818, pending filed Apr. 6, 1999 and a continuation-in-part of U.S. patent application Ser. No. 09/308,972, filed May 27, 1999, now U.S. Pat. No. 6,165,516, which is a nationalization of PCT/US96/18977, filed Nov. 27, 1996. Each of the foregoing applications are hereby incorporated by reference.

BACKGROUND OF THE INVENTION

The present invention relates to methods for producing chewing gum. More particularly, the invention relates to producing chewing gum containing an effective amount of an active medicament. Preferably, the active medicament is added to the chewing gum coating to control its rate of release from chewing gum and control the release of medicament for maximum effectiveness.

In recent years, efforts have been devoted to controlling release characteristics of various ingredients in chewing gum. Most notably, attempts have been made to delay the release of sweeteners and flavors in various chewing gum formulations to thereby lengthen the satisfactory chewing time of the gum. Delaying the release of sweeteners and flavors can also avoid an undesirable overpowering burst of sweetness or flavor during the initial chewing period. On the other hand, some ingredients have been treated so as to increase their rate of release in chewing gum.

Besides sweeteners, other ingredients may require a controlled release from chewing gum. In certain embodiments, it is contemplated that the active medicament that is added to the gum coating is generally released very readily. An active medicament may be added to the gum coating which is a water soluble matrix such that, during the chewing period, the medicament may be released quickly, resulting in a fast release. This would allow a chewing gum coating to be a carrier for an active medicament with these fast release characteristics.

It is of course known to provide active medicaments to individuals for various purposes. These medicaments can be used to treat diseases and as such are typically referred to as drugs or medicaments. Likewise, the drugs or medicaments can be used for preventive purposes. Still, it is known to provide medicaments to an individual for a variety of non-medical purposes including enhancing performance or maintaining health.

There are a great variety of such medicaments. These medicaments run the gamut from stimulants such as caffeine to drugs such as analgesics, tranquilizers, cardiovascular products, as well as vitamins, minerals, and supplements. Some such medicaments are taken on an "as-needed" basis while other medicaments must be taken at regular intervals by the individual.

Typically, drugs or medicaments are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation.

Oral administration of drugs is by far the most common method of moving drugs towards systemic circulation. When administered orally, drug absorption usually occurs due to the transport of cells across the membranes of the epithelial cells within the gastrointestinal tract. Absorption after oral administration is confounded by numerous factors. These factors include differences down the alimentary cannel in: the luminal pH; surface area per luminal volume; perfusion of tissue, bile, and mucus flow; and the epithelial membranes. See *Merck Manual* at page 2599.

A further issue affecting the absorption or orally administered drugs is the form of the drug. Most orally administered drugs are in the form of tablets or capsules. This is primarily for convenience, economy, stability, and patient acceptance. Accordingly, these capsules or tablets must be disintegrated or dissolved before absorption can occur. There are a variety of factors capable of varying or retarding disintegration of solid dosage forms. Further, there are a variety of factors that affect the dissolution rate and therefore determine the availability of the drug for absorption. See *Merck Manual* at page 2600.

When a drug rapidly dissolves from a drug product and readily passes across membranes, absorption from most site administration tends to be complete. This is not always the case for drugs given orally. Before reaching the vena cava, the drug must move down the alimentary canal and pass through the gut wall and liver, which are common sites of drug metabolism. Thus, the drug may be metabolized before it can be measured in the general circulation. This cause of a decrease in drug input is called the first pass effect. A large number of drugs show low bioavailabilities owning to an extensive first pass metabolism. The two other most frequent causes of low bioavailability are insufficient time in the GI tract and the presence of competing reactions. See *Merck Manual* at page 2602.

Bioavailability considerations are most often encountered for orally administered drugs. Differences in bioavailability can have profound clinical significance.

Although parenteral administration does provide a method for eliminating a number of the variables that are present with oral administration, parenteral administration is not a preferable route. Typically parenteral administration requires the use of medical personnel and is just not warranted nor practical for the administration of most agents and drugs, e.g., analgesics. Even when required, parenteral administration is objectionable due to patient concerns including comfort, infection, etc., as well as the equipment and costs involved.

There is therefore a need for an improved method of delivering drugs and other active agents to an individual.

SUMMARY OF THE INVENTION

The present invention provides improved methods for delivering a medicament or active agent to an individual. To this end, coated chewing gum products are provided including a medicament or active agent. The medicament or active agent is present within the coating of a chewing gum composition. It has been found that by adding the active agent to a gum coating, the medicament or active agent is quickly released from the chewing gum into saliva. Possibly, saliva coats the oral tissues under the tongue (sublingual)

and the sides of the mouth where the drug may partition from the saliva into the oral mucosa. Continuing to chew the chewing gum may create a pressure within the buccal cavity and may force the medicament or active agent or medicament directly into the systemic system of the individual through the oral mucosa contained in the buccal cavity. This may greatly enhance the transmucosal absorption of the drug into the systemic system as well as the bioavailability of the drug within the system.

Improved chewing gum products including medicaments and active agents in a gum coating are also provided by the present invention.

To this end, the present invention provides a method of drug delivery comprising the steps of: providing a chewing gum with a coating that includes a medicament in the chewing gum coating; chewing the chewing gum to cause the medicament to be released from the chewing gum coating into the buccal cavity of the chewer.

The active medicament may be any agent that is traditionally used as a medicament and lends itself to being administered through the oral cavity. Such active agents may be vitamins, cancer chemotherapeutics; antimycotics; oral contraceptives, nicotine or nicotine replacement agents, minerals, analgesics, antacids, muscle relaxants, antihistamines, decongestants, antibacterial agents, anesthetics, antitussives, diuretics, anti-inflammatories, antibiotics, AIDS medication, neurological drugs, antivirals, psychotherapeutic agents, anti-diabetic agents and cardiovascular agents, nutraceuticals and nutritional supplements.

Accordingly, an advantage of an embodiment of the present invention is to provide new methods for delivering medicaments or active agents to an individual.

Still further, an advantage of an embodiment of the present invention is to provide a method of delivering medicaments to an individual that provides for increase absorption and bioavailability as compared to medicaments that are designed to be absorbed in the GI tract.

Further, an advantage of an embodiment of the present invention is to provide a method of administering a medicament or agent to an individual at a lower level than is typically administered orally while still achieving the same effect.

Furthermore, an advantage of an embodiment of the present invention is to provide a method for administering drugs or agents to an individual that heretofore were administered parenterally.

Additionally, an advantage of an embodiment of the present invention is to provide a method of administering drugs that is more palatable than current methods.

Moreover, an advantage of an embodiment of the present invention is to provide an improved method for drug delivery.

The present invention also provides a method of producing chewing gum with active medicaments to control their release. Such active medicaments are added to a gum coating to deliver the active medicaments systemically. The present invention also relates to the chewing gum products so produced. Active medicaments may be added to sucrose-type gum formulations and sucrose-type coatings. The formulation may be a low or high moisture formulation containing low or high amounts of moisture containing syrup. Active medicaments may also be used in low or non-sugar gum formulations and coatings that use sorbitol, mannitol, other polyols or carbohydrates. Non-sugar formulations may include low or high moisture sugar-free chewing gums.

DETAILED DESCRIPTION OF THE PREFERRED EMBODIMENTS

The present invention provides improved methods for delivering medicaments and other active agents to an individual, as well as improved formulations including such medicaments and agents. Pursuant to the present invention, a medicament or active agent is contained in the coating of a chewing gum formulation, in contrast to some prior such formulations where the medicament or active agent is contained directly in the chewing gum composition.

Accordingly, as the chewing gum is chewed, the active agent is released into the saliva more quickly. During continual chewing, the medicament or active in the saliva may be then forced due to the pressure created by the chewing gum through the oral mucosa in the buccal cavity. The oral mucosa favors drug absorption. In contrast to a typically oral ingested drug, wherein the solution is in contact too briefly for absorption to be appreciable through the oral mucosa, it is believed that during the chewing, the active agent and/or medicament remains in the buccal cavity and may be forced or partitioned through the oral mucosa. An increase in the transmucosal absorption of the drug may be achieved as well as an increase in the bioavailability of the drug as compared to typical oral administration. The drug or active agent may be absorbed much quicker than if it was swallowed as in a typical oral administration. Indeed, the absorption approaches that of a parental administration and bioavailability may be also much greater than oral administration.

It is also possible that less medicament or active agent can be placed in the chewing gum coating than is typically orally administered to an individual to achieve an effect and the same bioequivalence can be achieved. In some instances, for certain drugs and agents, the administration of the medicament or agent using chewing gum through the buccal activity may provide an increase in therapeutic effect even as compared to parenteral administration.

For example, caffeine is commonly used as a stimulant to alleviate the effects of sleep deprivation. It is almost completely metabolized in the liver and therefore classified as a low clearance, flow independent drug. This means its rate of inactivation is unaffected by delivery to the liver and can only be modified by a change in the hepatic enzyme activity.

Data set forth in detail in U.S. patent application Ser. No. 09/386,818 herein incorporated by reference, suggests that the absorption rate constant (Ka) is significantly increased when caffeine is administrated through chewing gum versus a pill. This means that the caffeine is moving into the systemic circulation at a significantly faster rate. A similar change in the onset of dynamic response has also been noted, e.g., alertness and performance.

When caffeine is added to stick chewing gum at a level of about 0.2% to about 5%, caffeine imparts an intense bitterness to the chewing gum that lasts throughout the chewing period. The higher the level used, the stronger the bitterness. At about 0.2%, which is about 5 mg per 2.7 gram stick, the bitterness is below the threshold limit and is not readily discernible. Taste limits in stick chewing gum are generally about 0.4% (10 mg) to about 4% (100 mg) of caffeine in a stick of gum. The 60–80 mg level of caffeine is about the level of caffeine found in a conventional cup of coffee. The target level of caffeine in stick gum is about 40 mg per stick, with a range of about 25–60 mg, so that a five stick package of gum would contain about 200 mg of caffeine, or the equivalent of caffeine in two strong cups of coffee. However, at this level caffeine bitterness overwhelms the flavor initially and lasts throughout the chewing period.

For coated pellet gum, piece weight is generally about 1.5 grams per piece. However, one coated piece of gum is about equal to ½ piece of stick gum. Two pellets are equivalent to a stick of gum, and together weigh about 3 grams. The above-noted target level of 40 mg per stick is equivalent to 20 mg per coated piece, or a range of about 12 to 30 mg caffeine per piece. This is about 0.8% to about 2% caffeine in a piece of coated gum, or a target level of 1.3%.

Caffeine is a slightly water soluble substance and, therefore, has a moderately slow release from stick chewing gum. Caffeine is 2.1% soluble in water at room temperature, 15% soluble in water at 80° C. and 40% soluble in boiling water. This gives caffeine a moderately slow release as shown below:

| Chewing Time | % Caffeine Release |
|---|---|
| 0 min | — |
| 5 min | 56 |
| 10 min | 73 |
| 20 min | 88 |
| 40 min | 97 |

Generally, highly water soluble ingredients such as sugars in stick gum are about 80–90% released after only five minutes of chewing. For caffeine, only about 50% is released, while the other 50% remains in the gum after five minutes of chewing. After 20 minutes almost 90% of caffeine is released.

Even if caffeine is dissolved in hot water and mixed in the stick gum, when the gum is cooled or kept at room temperature, caffeine may return to its normal crystalline state and release at a rate similar to that shown above.

When an active such as caffeine is added to a gum coating, the active agent will have an increased water solubility, and release quickly into the mouth from the gum coating. Depending on the active agent, which may generally be non-water soluble, adding the active agent to a gum coating will increase the release of the active agent from chewing gum. Most water soluble active agents can be easily added to a gum coating to give a more uniform release from chewing gum. Depending on the active agent, the level released from the gum into the mouth can be adjusted for maximum effectiveness.

Other agents or medicaments may be included in the present invention. By the terms "active agent" the present invention refers to a compound that has a desired therapeutic or physiological effect once ingested and/or metabolized. The therapeutic effect may be one which decreases the growth of a xenobiotic or other gut flora or fauna, alters the activity of an enzyme, provides the physical relief from a malady (e.g., diminishes pain, acid reflux or other discomfort), has an effect on the brain chemistry of molecules that determine mood and behavior. Of course these are just examples of what is intended by therapeutic effect. Those of skill in the art will readily recognize that a particular agent has or is associated with a given therapeutic effect.

The active agent may be any agent that is traditionally used as a medicament and lends itself to being administered through the oral cavity. Such active agents may be vitamins, cancer chemotherapeutics, antimycotics, oral contraceptives, nicotine or nicotine replacement agents, minerals, analgesics, antacids, muscle relaxants, antihistamines, decongestants, anesthetics, antitussives, diuretics, anti-inflammatories, antibiotics, antivirals, psychotherapeutic agents, anti-diabetic agents, cardiovascular agents, bioengineered pharmaceuticals, nutraceuticals and nutritional supplements. Vitamins and co-enzymes that may be delivered using this invention include but are not limited to water or fat soluble vitamins such as thiamin, riboflavin, nicotinic acid, pyridoxine, pantothenic acid, biotin, flavin, choline, inositol and paraminobenzoic acid, carnitine, vitamin C, vitamin D and its analogs, vitamin A and the carotenoids, retinoic acid, vitamin E and vitamin K.

Examples of cancer chemotherapeutics agents include but are not limited to cisplatin (CDDP), procarbazine, mechlorethamine, cyclophosphamide, camptothecin, ifosfamide, melphalan, chlorambucil, bisulfan, nitrosurea, dactinomycin: daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

Antimicrobial agents that may be used include but are not limited to naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, P-lactamase inhibitors; meziocillin, piperacillin, aztreonam, norfloxacin, trimethoprim, ceftazidime, dapsone.

Antifungal agents that may be delivered include but are not limited to ketoconazole, fluconazole, nystatin, itraconazole, clomitrazole, and amphotericin B. Antiviral agents that may be used include but are not limited to acyclovir, trifluridine, idoxorudine, foscamet, ganciclovir, zidovudine, dideoxycytosine, dideoxyinosine, stavudine, famciclovir, didanosine, zalcitabine, rifimantadine, and cytokines.

Antacids include cimetidine, ranitidine, nizatidine, famotidine, omeprazole, bismuth antacids, metronidazole antacids, tetracylcine antacids, clarthromycin antacids, hydroxides of aluminum, magnesium, sodium bicarbonates, calcium bicarbonate and other carbonates, silicates, and phosphates.

Antihistamines are represented by but are not limited to cimetidine, ranitidine, diphenydramine, prylamine, promethazine, chlorpheniramine, chlorcyclizine, terfenadine, carbinoxamine maleate, clemastine fumarate, diphenhydramine hydrochloride, dimenhydrinate, prilamine maleate, tripelennamine hydrochloride, tripelennamine citrate, chlorpheniramine maleate, brompheniramine maleate, hydroxyzine pamoate, hydroxyzine hydrochloride, cyclizine lactate, cyclizine hydrochloride, meclizine hydrochloride, acrivastine, cetirizine hydrochloride, astemizole, levocabastine hydrochloride, and loratadine.

Decongestants and antitussives include agents such as dextromethorphan hydrobromide, levopropoxyphene napsylate, noscapine, carbetapentane, caramiphen, chlophedianol, pseudoephedrine hydrochloride, pseudoephedrine sulfate, phenylephidrine, diphenhydramine, glaucine, pholcodine, and benzonatate.

Anesthetics include etomidate, ketamine, propofol, and benodiazapines (e.g., chlordiazepoxide, diazepame, clorezepate, halazepam, flurazepam, quazepam, estazolam, triazolam, alprozolm, midazolam, temazepam, oxazepam, lorazepam), benzocaine, dyclonine, bupivacaine, etidocaine, lidocaine, mepivacaine, promoxine, prilocaine, procaine, proparcaine, ropivacaine, tetracaine. Other useful agents may include amobartital, aprobarbital, butabarbital, butalbital mephobarbital, methohexital, pentobarbital, phenobarbital, secobarbital, thiopental, paral, chloralhydrate, ethchlorvynol, clutethimide, methprylon, ethinamate, and meprobarnate.

Analgesics include opioids and other medicaments such as morphine, mepidine, dentanyl, sufentranil, alfentanil, aspirin, acetaminophen, ibuprofen, indomethacine, naproxen, atrin, isocome, midrin, axotal, firinal, phrenilin, ergot, and ergot derivatives (wigraine, cafergot, ergostat, ergomar, dihydroergotamine), imitrex, and ketoprofen.

Diuretics include but are not limited to acetazolamide, dichlorphenamide, methazolamide, furosemide, bumetanide, ethacrynic acid torseimde, azosemide, muzolimine, piretanide, tripamide, bendroflumethiazide, benzthiazide, chlorothiazide, hydrochlorothiazide, hydroflumethiazide, methyclothiazide, polythiazide, trichlormethiazide, indapamide, metolazone, quinethazone, amiloride, triamterene, sprion olactone, canrenone, and potassium canrenoate.

Anti-inflammatories include but are not limited to salicylic acid derivatives (e.g. aspirin), indole and indene acetic acids (indomethacin, sulindac and etodalac) heteroaryl acetic acids (tolmetin diclofenac and ketorolac) aryl propionic acid derivatives (ibuprofen, naproxen, ketoprofen, fenopren, oxaprozine), anthranilic acids (mefenamic acid, meclofenamic acid) enolic acids (piroxicam, tenoxicam, phenylbutazone and oxyphenthatrazone).

Psychotherapeutic agents include thorazine, serentil, mellaril, millazinetindal, permitil, prolixin, trilafon, stelazine, suprazine, taractan, navan, clozaril, haldol, halperon, loxitane, moban, orap, risperdal, alprazolam, chordiaepoxide, clonezepam, clorezepate, diazepam, halazepam, lorazepam, oxazepam, prazepam, buspirone, elvavil, anatranil, adapin, sinequan, tofranil, surmontil, asendin, norpramin, pertofrane, ludiomil, pamelor, vivactil, prozac, luvox, paxil, zoloft, effexor, wellbutrin, serzone, desyrel, nardil, parnate, eldepryl.

Cardiovascular agents include but are not limited to nitroglycerin, isosorbide dinitrate, sodium nitroprisside, captopril, enalaprill, enalaprilat, quinapril, lisinopril, ramipril, losartan, amrinone, linnone, vesnerinone, hydralazine, nicorandil, prozasin, doxazosin, bunazosin, tamulosin, yohimbine, propanolol, metoprolol, nadolol, atenolol, timolol, esmolol, pindolol, acebutolol, labetalol, phentolamine, carvedilol, bucindolol, verapamil, nifedipine, amlodipine and dobutamine, or a sexual dysfunction agent like sildenafil citrate (Viagra).

It is envisioned that depending on the active agent or medicament, the resultant chewing gum can be used to treat inter alia: coughs, colds, motion sickness; allergies; fevers; pain; inflammation; sore throats; cold sores; migraines; sinus problems; diarrhea; diabetes, gastritis; depression; anxiety, hypertension; angina and other maladies and symptoms. Also these gums may be useful in ameliorating cravings in substance abuse withdrawal or for appetite suppression. Specific active agents or medicaments include by way of example and limitation: caffeine, aspirin, acetaminophen; ibuprofen; ketoprofen; cimetidine, ranitidine, famotidine, dramamine, omeprazole, dyclonine hydrochloride, chlorpheniramine maleate, pseudoephedrine hydrochloride, dextromethorphan hydrobromide, benzocaine, sodium naproxen, and nicotine.

Compositions that may be formulated into a suitable chewing gum formulation are described in, for examples, U.S. Pat. Nos. 5,858,423; 5,858,413; 5,858,412 and 5,858,383. Additionally, Goodman and Gilman's "The Pharmaceutical Basis of Therapeutics" (Eds. Hardman et al., Publ. McGraw Hill, N.Y.) provides comprehensive guidance of useful drugs and their mechanisms of action. Medicated chewing gums have been particularly effective in the delivery of agents such as nicotine as described in, for example, U.S. Pat. Nos. 5,866,179; and 5,889,028. U.S. Pat. No. 5,846,557 describes general chewing gum compositions containing cough suppressing agents. These patents are incorporated herein by reference as providing a teaching of the incorporation of medicinal agents into oral chewable formulations. It should be understood that the present chewing gum formulation(s) and coatings are not limited to the agents listed herein above, indeed any medicinal or other active agent that lends itself to ingestion may be formulated into the chewing gum coatings and used in the present invention.

Nutraceuticals and nutritional supplements may also be added to chewing gums as well as the gum coatings as active agents. Among these are herbs and botanicals that include, but are not limited to capsicum, chamomile, cat's claw, echinacea, garlic, ginger, ginko, various ginseng, green tea, golden seal, kava kava, nettle, passion flower, saw palmetto, St. John's wort, and valerian. Also included are mineral supplements such as calcium, copper, iodine, iron, magnesium, manganese, molybdenum, phosphorous, selenium and zinc. Other nutraceuticals that also can be added to chewing gum as active agents are benzoin, fructo-oligosaccharides, glucosamine, grapeseed extract, guarana, inulin, phosphotidylserine, phytosterols, phytochemicals, isoflavones, lecithin, lycopene, oligofructose, polyphenol and psyllium as well as weight loss agents such as chromium picolinate and phenylpropanolamine.

Preferably, the agents or medicaments are contained in the chewing gum coating at levels of approximately 12 micrograms to 250 milligrams per gram of gum product (core plus coating weight). The specific levels will depend on the active ingredient. For example, if chromium picolinate is the active ingredient in an embodiment, it would be present at a level of 50 micrograms per serving (1.5 grams per pellet of gum); aspirin would be preset at a level of 325 milligrams per 1.5/gram serving (pellet).

While the present invention is particularly directed to the use of active agents in chewing gum coatings, it is also recognized that there may be a benefit in having a part of the active agent in the chewing gum formulation. The level of medicament or agent in the chewing gum formulation and in the coating is selected so as to create, when the gum is chewed, a sufficiently high concentration of the medicament or agent in the saliva.

For example, when the agent is a stimulant such as nicotine or caffeine, the level of the stimulant in the chewing gum and coating should be such that it creates a saliva content of stimulant of approximately 15 to 440 ppm when the chewing gum is chewed for 2 minutes. At this level, a sufficient amount of stimulant will be delivered to the chewer to create desired therapeutic effects. If a medicament is used such as a medicinal agent (e.g., analgesics), sufficient medicinal agent should be present in the chewing gum and coating to create a saliva content of approximately 1700 to approximately 4400 ppm after the chewing gum product has been chewed for 2 minutes. For botanical agents (e.g., chamomile, kava, kola, nut, ginseng, and Echinacea), the agent should be present in a sufficient amount to create a saliva content of approximately 85 to 1100 ppm when the chewing gum product is chewed for 2 minutes. For a metabolizer, for example, chromium picolinate and hydroxichitic acid, the agents should be present in an amount to create a saliva content of approximately 0.5 to about 900 ppm when chewed for at least two minutes. If the agent is a vitamin or mineral (e.g., phosphatidy serine, vitamin C, and zinc), the agent should be present in the amount to create a saliva content of the vitamin or mineral of approximately 10 to about 250 ppm when chewed for 2 minutes.

Pursuant to the present invention, depending on the agent or medicament, the dosing regiment will change. For example, if the medicament is an analgesic, the chewing gum product would be taken on an "as-needed" basis. Of course, similar to the oral administration of an analgesic, there would be restrictions on the number of pieces of chewing gum product chewed, for example, not more often than one pellet every four hours and not more often than four to five times a day. If the agent is a stimulant such as caffeine to be used to enhance performance than the chewing gum product would be chewed, in a preferred embodiment ten minutes or less before the performance.

The medicament or agent can be contained in coatings on a variety of different chewing gum compositions. Referring now to the chewing gum, pursuant to the present invention the chewing gum may be based on a variety of different chewing gums that are known. For example, the chewing gums can be low or high moisture, sugar or sugarless, wax containing or wax free, low calorie (via high base or low calorie bulking agents), and/or may contain dental agents.

Active agents may be added to the gum coating along with sweeteners, more specifically high-intensity sweeteners such as thaumatin, dihydrochalcones, acesulfame K, aspartame, N-substituted APM derivatives such as neotame, sucralose, alitame, saccharin and cyclamates. These can also have the effect of reducing unpleasant tastes such as bitterness. Additional bitterness inhibitors or taste maskers can also be combined with active agents and sweeteners to give a reduced unpleasant taste.

Medicament actives may also be combined in a coated chewing gum product. A single active may be added to a gum coating for fast release and also added to the gum center with or without encapsulation for slow release. If the active has an affinity for the gum base, it may naturally give a slow release without encapsulation. If the active is fast release, it would have to be encapsulated or entrapped for the desired time release.

A combination of medicament actives may be used in the gum coating and in the gum center for various reasons. In some cases, medicaments may be reactive to one another and should be kept form coming in contact with each other. In other cases, combinations of medicaments may be used for various symptoms where multiple medicaments may be effective. For example, a decongestant such as pseudoephedrine may be added to a gum coating and an antihistamine such as chlorpheniramine may be added to a gum center to treat cold/allergy symptoms. For sore throat, an oral anesthetic like dyclonine hydrochloride may be used in the gum coating and an antibacterial agent like cetyl pyridinium chloride may be added to a gum center. Additionally, any other materials like dextromethorphan hydrobromide for cough relief or an analgesic like ketoprofen may be added to either a gum coating and a gum center for cold symptoms. Other combinations of medicament active agents for other types of ailments are also within the scope of this invention.

In many instances, active medicaments may have a low quality off-taste or bitterness, if added to a chewing gum coating. In most cases, this off taste may be masked with high intensity sweeteners, but in other instances, a bitterness inhibitor may be needed to reduce a bitter taste of a medicament.

There are a wide variety of bitterness inhibitors that can be used in food products as well as with active agents. Some of the preferred bitterness inhibitors are the sodium salts which are discussed in the article *Suppression of Bitterness by Sodium: Variations Among Bitter Taste Stimuli*, by R. A. S. Breslin and G. K. Beceuchenp from Monell Chemical Senses Center, Philadelphia, Pa. Sodium salts discussed are sodium acetate and sodium gluconate. Other sodium salts that may also be effective are sodium glycinate, sodium ascorbate and sodium glycerolphosphate. Among these, the most preferred is sodium gluconate and sodium glycinate since they have a low salty taste and are most effective to reduce bitterness of most active medicaments.

Most of the sodium salts are very water soluble and are readily released from chewing gum coating to function as bitterness inhibitors. In most instances, the sodium salts which release readily from chewing gum center may be modified by encapsulation to give an even faster release from chewing gum. However, in some instances the sodium salts would be encapsulated or entrapped to give a delayed release from gum. Generally, the bitterness inhibitor should release with the active medicament for maximum effectiveness.

Release of the medicament from gum coating may also be effected by particle size of the medicament. Small particles release more quickly whereas large particles more slowly. Fast release can also be accomplished by dissolving medicament in a liquid and used in a gum coating. Medicaments may be dissolved in solvents, flavors, or other transdermal vehicles used as absorption enhancing agents and added to gum or to a gum coating. These absorption enhancing agents may also be added to the gum or gum coating separately from the active ingredient. Their presence may help volatilize medicaments or allow increased transmucosal absorption of the active agent through the nasal mucosa or the lungs. These solvents, flavors, or transdermal vehicles may transport medicaments faster through the oral mucosa.

Faster absorption may be affected by increasing flavor levels as well as the addition of other flavor components, such as menthol and menthol derivatives, limonene, carvone, isomenthol, eucalyptol, menthone, pynene, camphor and camphor derivatives, as well as monoterpene natural products, monoterpene derivatives, and sesquaterpenes, including caryophyllene and copaene. Other vehicles that may be used to increase transdermal absorption are: ethanol, polyethylene glycol, 2-pyrrolidones, myristic acid, Brij-35 (surfactant), p-phenyl phenol, nitrobenzene, stearyl alcohol, cetyl alcohol, croton oil, liquid paraffin, dimethyl sulfoxide (DMSO), non-ionic surfactants, liposomes, lecithin fractions, and long chain amphipathic molecules (molecules with polar or non-ionized groups on one end and non-polar groups at the other end).

Tableting of chewing gum is disclosed in U.K. Patent Publication No. 1,489,832; U.S. Pat. No. 4,753,805; EP Patent Publication No. 0 221 850; and Italy Patent Publication No. 1,273,487. These patents disclose active agents added to chewing gum which is then tableted. As an embodiment of this invention, active agents may be encapsulated or entrapped and added to a chewing gum formulation which is then tableted and used as a core for a coated chewing gum pellet that is coated with a sugar, polyol or film that includes an active agent. The chewing gum core may contain one active agent or multiple active medicaments and the coating may contain one or a plurality of active medicaments. This form will yield unique chewing gum products.

In general, a chewing gum composition typically comprises a water-soluble bulk portion, a water-insoluble chewable grams base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, softeners and inorganic fillers. The gum base may or may not include wax. The insoluble gum base can constitute approximately 5% to about 95% by weight of the chewing gum, more commonly the gum base comprises 10% to about 50% of the gum, and in some preferred embodiments approximately 25% to about 35% by weight, of the chewing gum.

In a particular embodiment, the chewing gum base of the present invention contains about 20% to about 60% by weight synthetic elastomer, about 0% to about 30% by weight natural elastomer, about 5% to about 55% by weight elastomer plasticizer, about 4% to about 35% by weight filler, about 5% to about 35% by weight softener, and optional minor amounts (about 1% or less by weight) of miscellaneous ingredients such as colorants, antioxidants, etc.

Synthetic elastomers may include, but are not limited to, polyisobutylene with GPC weight average molecular weight of about 10,000 to about 95,000, isobutylene-isoprene copolymer (butyl elastomer), styrene-butadiene, copolymers having styrene-butadiene ratios of about 1:3 to about 3:1, polyvinyl acetate having GPC weight average molecular weight of about 2,000 to about 90,000, polyisoprene, polyethylene, vinyl acetate-vinyl laurate copolymer having vinyl laurate content of about 5% to about 50% by weight of the copolymer, and combinations thereof.

Preferred ranges for polyisobutylene are 50,000 to 80,000 GPC weight average molecular weight and for styrene-butadiene are 1:1 to 1:3 bound styrene-butadiene, for polyvinyl acetate are 10,000 to 65,000 GBC weight average molecular weight with the higher molecular weight polyvinyl acetates typically used in bubble gum base, and for vinyl acetate-vinyl laurate, vinyl laurate content of 10–45%.

Natural elastomers may include natural rubber such as smoked or liquid latex and guayule as well as natural gums such as jelutong, lechi caspi, perillo, sorva, massaranduba balata, massaranduba chocolate, nispero, rosindinha, chicle, gutta hang kang, and combinations thereof. The preferred synthetic elastomer and natural elastomer concentrations vary depending on whether the chewing gum in which the base is used is adhesive or conventional, bubble gum or regular gum, as discussed below. Preferred natural elastomers include jelutong, chicle, sorva and massaranduba balata.

Elastomer plasticizers may include, but are not limited to, natural rosin esters such as glycerol esters or partially hydrogenated rosin, glycerol esters of polymerized rosin, glycerol esters of partially dimerized rosin, glycerol esters of rosin, pentaerythritol esters of partially hydrogenated rosin, methyl and partially hydrogenated methyl esters of rosin, pentaerythritol esters of rosin; synthetics such as terpene resins derived from alpha-pinene, beta-pinene, and/or d-limonene; and any suitable combinations of the foregoing. The preferred elastomer plasticizers will also vary depending on the specific application, and on the type of elastomer which is used.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as wood, and combinations thereof.

Softeners/emulsifiers may include tallow, hydrogenated tallow, hydrogenated and partially hydrogenated vegetable oils, cocoa butter, glycerol monostearate, glycerol triacetate, lecithin, mono-, di- and triglycerides, acetylated monoglycerides, fatty acids (e.g. stearic, palmitic, oleic and linoleic acids), and combinations thereof Colorants and whiteners may include FD&C-type dyes and lakes, fruit and vegetable extracts, titanium dioxide, and combinations thereof.

The base may or may not include wax. An example of a wax-free gum base is disclosed in U.S. Pat. No. 5,286,500, the disclosure of which is incorporated herein by reference.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, N-substituted APM derivatives such as neotame, salts of acesulfame, altitame, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; Raftilose, Raftilin; fructooligosaccharides (NutraFlora); palatinose oligosaccharide; guar gum hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

In general, chewing gum is manufactured by sequentially adding the various chewing gum ingredients to a commercially available mixer known in the art. After the ingredients have been thoroughly mixed, the gum mass is discharged from the mixer and shaped into the desired form such as rolling sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

In this invention, medicaments or actives are used in the coating/panning of a pellet chewing gum. Pellet or ball gum is prepared as conventional chewing gum but formed into pellets that are pillow shaped, or into balls. The pellets/balls can be then sugar coated or panned by conventional panning techniques to make a unique coated pellet gum. The active agent may be soluble in flavor or can be blended with other powders often used in some types of conventional panning procedures. Active agents are isolated from other gum ingredients which modifies its release rate from chewing gum. Levels of actives may be about 10 ppm to 30% by weight of chewing gum coating. The weight of the coating may be about 20% to about 50% of the weight of the finished product, but may be as much as 75% of the total gum product. The active level will be based on the dosage for one or two pellets.

Conventional panning procedures generally coat with sucrose, but recent advances in panning have allowed use of other carbohydrate materials to be used in place of sucrose. Some of these components include, but are not limited to, dextrose, maltose, palatinose, xylitol, lactitol, hydrogenated isomaltulose, erythritol, maltitol, and other new alditols or combinations thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetables gums like alginates, locust bean gum, guar gum, and gum tragacanth, insoluble carbonates like calcium carbonate or magnesium carbonate and talc. Antitack agents may also be added as panning modifiers, which allow the use of a variety of carbohydrates and sugar alcohols to be used in the development of new panned or coated gum products. Flavors may also be added with the sugar or sugarless coating and with the active to yield unique product characteristics.

Another type of pan coating could also isolate the active agent from the chewing gum ingredients. This technique is referred to as a film coating and is more common for pharmaceuticals than in chewing gum, but procedures are similar. A film like shellac, zein, or cellulose type material is applied onto a pellet-type product forming a thin film on the surface of the product. The film is applied by mixing the polymer, plasticizer and a solvent (pigments are optional) and spraying the mixture onto the pellet surface. This is done in conventional type panning equipment, or in more advanced side-vended coating pans. Since most active agents may be alcohol soluble, they may be readily added with this type of film. When a solvent like an alcohol is used, extra precautions are needed to prevent fires and explosions, and specialized equipment must be used.

Some film polymers can use water as the solvent in film coating. Recent advances in polymer research and in film coating technology eliminates the problem associated with the use of solvents in coating. These advances make it possible to apply aqueous films to a pellet or chewing gum product. Some active agents can be added to this aqueous film or even the alcohol solvent film, in which an active agent is highly soluble. This film may also contain a flavor along with a polymer and plasticizer. The active agent can also be dissolved in the aqueous or non-aqueous solvent and coated on the surface with the aqueous film. In some instances a combination of film and sugar or polyol coating may be useful, especially if the active is added with the film coating material. Also the film coating may be applied early, middle, or late in the coating process. This will give a unique release of active agent from a film-coated product.

After a coating film with an active medicament is applied to a chewing gum product, a hard shell sugar or polyol coating may then be applied over the film coated product. In some instances a soft shell sugar or polyol coating may also be used over the film coated product. The level of film coating applied to a pellet gum may be generally from about 0.5% to about 3% of the gum product. The level of overcoating of the hard or soft shell may be about 20% to about 75%. When the active agent is added with the film coating and not with the sugar/polyol coating, better control of the amount of active agent in the product may be obtained. In addition, the sugar/polyol overcoating may give an improved stability to the active agent in the product.

As noted above, the coating may contain ingredients such as flavoring agents, as well as artificial sweeteners and dispersing agents, coloring agents, film formers and binding agents. Flavoring agents contemplated by the present invention include those commonly known in the art such as essential oils, synthetic flavors or mixtures thereof, including but not limited to oils derived from plants and fruits such as citrus oils, fruit essences, peppermint oil, spearmint oil, other mint oils, clove oil, oil of wintergreen, anise and the like. The flavoring agents may be used in an amount such that the coating will contain from about 0.2% to about 3% flavoring agent, and preferably from about 0.7% to about 2.0% flavoring agent. Active agents may be preblended with the flavor used in coating.

Artificial sweeteners contemplated for use in the coating include but are not limited to synthetic substances, saccharin, thaumatin, alitame, saccharin salts, aspartame, N-substituted APM derivatives such as neotame, sucralose and acesulfame-K. The artificial sweetener may be added to the coating syrup in an amount such that the coating will contain from about 0.01% to about 0.5%, and preferably from about 0.1% to about 0.3% artificial sweetener.

Dispersing agents are often added to syrup coatings for the purpose of whitening and tack reduction. Dispersing agents contemplated by the present invention to be employed in the coating syrup include titanium dioxide, talc, or any other antistick compound. Titanium dioxide is a presently preferred dispersing agent of the present invention. The dispersing agent may be added to the coating syrup in amounts such that the coating will contain from about 0.1% to about 1.0%, and preferably from about 0.3% to about 0.6% of the agent.

Coloring agents are preferably added directly to the syrup in the dye or lake form. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. Binding agents may be added either as an initial coating on the chewing gum center or may be added directly into the syrup. Binding agents contemplated by the present invention include gum arabic, gum talha (another type of acacia), alginate, cellulosics, vegetable gums and the like.

The coating is initially present as a liquid syrup which contains from about 30% to about 80% or 85% of the coating ingredients previously described herein, and from about 15% or 20% to about 70% of a solvent such as water. In general, the coating process is carried out in a rotating pan. Sugar or sugarless gum center tablets to be coated are placed into the rotating pan to form a moving mass.

The material or syrup which will eventually form the coating is applied or distributed over the gum center tablets. Flavoring agents may be added before, during and after applying the syrup to the gum centers. Once the coating has dried to form a hard surface, additional syrup additions can be made to produce a plurality of coatings or multiple layers of hard coating.

In a hard coating panning procedure, syrup is added to the gum center tablets at a temperature range of from about 100° F. to about 240° F. Mostly, the syrup temperature is from about 130° F. to about 200° F. throughout the process in order to prevent the polyol or sugar in the syrup from crystallizing. The syrup may be mixed with, sprayed upon, poured over, or added to the gum center tablets in any way known to those skilled in the art.

In general, a plurality of layers is obtained by applying single coats, allowing the layers to dry, and then repeating the process. The amount of solids added by each coating step depends chiefly on the concentration of the coating syrup. Any number of coats may be applied to the gum center tablet. Generally, no more than about 75–100 coats are applied to the gum center tablets. The present invention contemplates applying an amount of syrup sufficient to yield a coated comestible containing about 10% to about 75% coating. Where higher dosage of an active agent is needed, the final product may be higher than 75% coating.

Those skilled in the art will recognize that in order to obtain a plurality of coated layers, a plurality of premeasured aliquots of coating syrup may be applied to the gum center tablets. It is contemplated, however, that the volume of aliquots of syrup applied to the gum center tablets may vary throughout the coating procedure.

Once a coating of syrup is applied to the gum center tablets, the present invention contemplates drying the wet syrup in an inert medium. A preferred drying medium comprises air. Forced drying air contacts the wet syrup coating in a temperature range of from about 70° to about 115° F. Generally, the drying air is in the temperature range of from about 80° to about 100° F. The invention also contemplates that the drying air possess a relative humidity of less than about 15 percent. Preferably, the relative humidity of the drying air is less than about 8 percent.

The drying air may be passed over and admixed with the syrup coated gum centers in any way commonly known in the art. Generally, the drying air is blown over and around or through the bed of the syrup coated gum centers at a flow rate, for large scale operations, of about 2800 cubic feet per minute. If lower quantities of material are being processed, or if smaller equipment is used, lower flow rates would be used.

For many years, flavors have been added to a sugar coating of pellet gum to enhance the overall flavor of gum. These flavors include spearmint flavor, peppermint flavor, wintergreen flavor, and fruit flavors. These flavors are generally preblended with the coating syrup just prior to applying it to the core or added together to the core in one or more coating applications in a revolving pan containing the cores. Generally, the coating syrup is very hot, about 130° to 200° F., and the flavor may volatilize if preblended with the coating syrup too early.

The concentrated coating syrup is applied to the gum cores as a hot liquid, the sugar or polyol allowed to crystallize, and the coating then dried with warm, dry air. This is repeated in about 30 to 100 applications to obtain a hard shell coated product having an increased weight gain of about 40% to 75%. A flavor is applied with one, two, three or even four or more of these coating applications. Each time flavor is added, several non-flavored coatings are applied to cover the flavor before the next flavor coat is applied. This reduces volatilization of the flavor during the coating process.

For mint flavors such spearmint, peppermint and wintergreen, some of the flavor components are volatilized, but sufficient flavor remains to give a product having a strong, high impact flavor. Fruit flavors, that may contain esters, are more easily volatilized and may be flammable and/or explosive and therefore, generally these type of fruit flavors may be pretreated in order to be able to add them to a gum coating.

In an embodiment of this invention, an active agent is preblended with a gum arabic solution to become a paste and then applied to the cores. To reduce stickiness, the preblend may be mixed with a small amount of coating syrup before being applied. Forced air drying is then continued as the gum arabic binds the active agent to the cores. Then additional coatings are applied to cover the active agent and imbed the treated active agent in the coatings.

GUM FORMULATION EXAMPLES

The following examples of the invention and comparative examples are provided by way of explanation and illustration.

As noted earlier, the gum formulas can be prepared as sugar or sugarless type formulations. These formulas are made in a pellet or pillow shape pellet or a round ball or any other shape of product for coating/panning. However, gum formulas for pellet centers are generally adjusted to a higher level of gum base than stick gum to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 40% gum base with a corresponding decrease in the other ingredients except flavor. Even higher levels of base may be used when an active is added to a pellet coating. Generally flavors increase with the level of gum base as the base tends to bind flavors into the gum and more flavor is needed to give a good flavorful product. However flavors can also be added to the coating to give increased flavor impact and more flavor perception.

A wide range of changes and modifications to the embodiments of the invention described above will be apparent to persons skilled in the art. While the invention is described with respect to hard-coated chewing gum, it will be appreciated that the process is applicable to coating other food products, such as candies, in which a coating with dyclonine hydrochloride would have utility.

Examples

The following examples of the invention and comparative examples are provided by way of explanation and illustration.

The formulas listed in Table 1 comprise various sugar-type formulas in which active medicament can be added to gum coating after it is dissolved in water or mixed with various aqueous solvents. Dyclonine hydrochloride is an active medicament used as an oral anesthetic for sore throat.

Various gum formulas may be made in a pellet or pillow shape pellet or a round ball or any other shape of product for coating/panning. As noted earlier, gum formulas are generally adjusted to a higher level of gum base to give a more consumer acceptable size of gum bolus.

Some typical sugar type gum center formulations are shown in Table 1. Gum center formulas may or may not contain dyclonine hydrochloride.

TABLE 1

(WEIGHT PERCENT)

|  | EX. 1 | EX. 2 | EX. 3 | EX. 4 | EX. 5 | EX. 6 |
|---|---|---|---|---|---|---|
| SUGAR | 52.0 | 48.7 | 47.55 | 44.0 | 40.7 | 38.55 |
| GUM BASE | 26.0 | 30.0 | 35.00 | 26.0 | 30.0 | 35.00 |
| CORN SYRUP | 20.0 | 19.0 | 15.00 | 18.0 | 17.0 | 14.00 |
| GLYCERIN | 1.0 | 1.0 | 1.00 | 1.0 | 1.0 | 1.00 |
| PEPPERMINT FLAVOR | 1.0 | 1.0 | 1.00 | 1.0 | 1.0 | 1.00 |
| DEXTROSE MONOHYDRATE | — | — | — | 10.0 | 10.0 | 10.00 |
| DYCLONINE HYDROCHLORIDE | — | 0.3 | 0.45 | — | 0.3 | 0.45 |

Gum center formulations with or without active dyclonine hydrochloride can also be made similar to other formulations for low, medium, and high moisture formulas. Higher levels of base may be used with a corresponding decrease in other ingredients. Also, other sugars and polyols may be used in the gum centers. Dyclonine hydrochloride may be added to a gum center only, or to a gum coating with none in the center, or to both center and coating. Coated gum pieces are about 1.5 grams, so to obtain 3 mg of dyclonine hydrochloride total piece must contain 0.2%.

Dyclonine hydrochloride can then be used in the coating formula on the various pellet gum formulations. The following Table 2 shows some sugar and dextrose type formulas:

TABLE 2

(DRY WEIGHT PERCENT)

|  | EX. 7 | EX. 8 | EX. 9 | EX. 10 | EX. 11 | EX. 12 |
|---|---|---|---|---|---|---|
| SUGAR | 97.0 | 95.2 | 93.5 | 96.8 | 94.9 | 93.0 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| DYCLONINE HYDROCHLORIDE | 0.1 | 0.2 | 0.6[a] | 0.1 | 0.2 | 0.6[a] |

|  | EX. 13 | EX. 14 | EX. 15 | EX. 16 |
|---|---|---|---|---|
| DEXTROSE MONOHYDRATE | 97.5 | 95.2 | 97.0 | 93.9 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| DYCLONINE HYDROCHLORIDE | 0.1 | 0.2 | 0.2 | 0.6[a] |

[a] All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. Some of the dextrose may be added as a dry charge which may also contain the active agent. Dyclonine hydrochloride may be dissolved in water, not mixed with hot syrup, but added between coatings, or it may be added to the hot syrup and used in the early stages of coating or used throughout the coating process. Flavor is not mixed with the hot syrup, but added at low levels with one or more coats. Dyclonine hydrochloride may be dissolved in flavor and added to the coating. After the final coats are applied and dried, wax is applied to give a smooth polish.

Dyclonine hydrochloride may also be used in coating of sugarless gum centers. Like sugar gum centers, the base formulation can be increased in proportion to the amount of coating applied to the center. Formulations with and without dyclonine hydrochloride for low and high moisture gum can be used to make gum centers. Generally, the base level may be increased to 30–46% with the other ingredients proportionally reduced. Some typical gum formulas are in Table 3.

TABLE 3

(WEIGHT PERCENT)

|  | EX. 17 | EX. 18 | EX. 19 | EX. 20 | EX. 21 | EX. 22 | EX. 23 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 45.0 | 45.9 | 40.3 | 44.5 | 41.4 | 26.1 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| ACTIVE DYCLONINE HYDROCHLORIDE[b] | — | 0.3 | 0.4 | — | 0.3 | 0.3 | 0.4 |

[a] Lycasin brand hydrogenated starch hydrolyzate used instead of sorbitol liquid
[b] This material may be dissolved in water, glycerin, sorbitol liquid, or HSH.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Dyclonine hydrochloride may be used in sugarless coatings with xylitol, sorbitol, maltitol, lactitol, hydrogenated isomaltulose and erythritol. The following table gives formulas for a xylitol coating:

TABLE 4

(DRY WEIGHT PERCENT)

| | EX. 24 | EX. 25 | EX. 26 | EX. 27 | EX. 28 | EX. 29 |
|---|---|---|---|---|---|---|
| XYLITOL | 94.7 | 92.2 | 90.1 | 90.0 | 89.7 | 88.2 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| DYCLONINE HYDROCHLORIDE | 0.1 | 0.2 | 0.6a) | 0.1 | 0.2 | 0.6a) |

*Lake color dispersed in xylitol solution
**Calcium carbonate used in place of titanium dioxide
a)All of the active agent is in the gum coating, which comprises 33% of the gum product.

The above formulas are used to coat pellets by applying a xylitol/gum arabic solution in multiple coats and air drying. Color or whitener is also mixed in the solution. Dyclonine hydrochloride may be dissolved in water and added between coating applications or mixed with the hot syrup and used in the early stages of coating or used throughout the coating process. After pellets have been coated and dried, talc and wax are added to give a polish.

For coating formulas based on sorbitol, maltitol, lactitol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 5

(DRY WEIGHT PERCENT)

| | EX. 30 | EX. 31 | EX. 32 | EX. 33 | EX. 34 | EX. 35 |
|---|---|---|---|---|---|---|
| MALTITOL | 96.7 | 94.7 | 91.5 | 86.7 | 75.9 | 68.9 |
| MALTITOL POWDER | — | — | — | 10.0 | 20.0 | 25.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| DYCLONINE HYDROCHLORIDE | 0.1 | 0.2 | 0.6a) | 0.1 | 0.2 | 0.6a) | a)All of the active agent is in the coating, which comprises 33% of the product.

Maltitol powder is used to dry charge in the early stages of coating. Maltitol, gum arabic, and whitener are blended into a syrup and applied to pellets. Dyclonine hydrochloride may be applied in a similar manner as in the previous xylitol coating or may be preblended with the dry charge material. After all coating is applied and dried, talc and wax are added to give a polish.

In a similar manner, coatings with sorbitol, lactitol, and hydrogenated isomaltulose may be made in the coating formulas in Table 5 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge, along with the active medicament.

Some polyols such as sorbitol, maltitol, lactitol, erythritol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Some typical sugar type gum center formulations are shown in Table 6 with chlorpheniramine maleate. Chlorpheniramine maleate is an active medicament used as an antihistamine. Gum center formulas may or may not contain chlorpheniramine maleate.

TABLE 6

(WEIGHT PERCENT)

| | EX. 36 | EX. 37 | EX. 38 | EX. 39 | EX. 40 | EX. 41 |
|---|---|---|---|---|---|---|
| SUGAR | 52.0 | 48.73 | 47.59 | 44.0 | 40.73 | 38.59 |
| GUM BASE | 26.0 | 30.0 | 35.00 | 26.0 | 30.0 | 35.00 |
| CORN SYRUP | 20.0 | 19.0 | 15.00 | 18.0 | 17.0 | 14.00 |
| GLYCERIN | 1.0 | 1.0 | 1.00 | 1.0 | 1.0 | 1.00 |

TABLE 6-continued (WEIGHT PERCENT)

|  | EX. 36 | EX. 37 | EX. 38 | EX. 39 | EX. 40 | EX. 41 |
|---|---|---|---|---|---|---|
| PEPPERMINT FLAVOR | 1.0 | 1.0 | 1.00 | 1.0 | 1.0 | 1.00 |
| DEXTROSE MONO-HYDRATE | — | — | — | 10.0 | 10.0 | 10.00 |
| ACTIVE CHLORPHEN-IRAMINE MALEATE | —[a] | 0.27 | 0.41 | —[a] | 0.27 | 0.41 |

[a]All of the active agent is in the coating, which comprises 33% of the product.

Gum center formulations with or without active chlorpheniramine maleate can also be made similar to other formulations for low, medium, and high moisture formulas. Higher levels of base may be used with a corresponding decrease in other ingredients. Also, other sugars are polyols may be used in the gum centers. Chlorpheniramine maleate may be added to a gum center only, or to a gum coating with none in the center, or to both center and coating. Coated gum pieces are about 1.5 grams, so to obtain 4 mg of chlorpheniramine maleate total piece must contain 0.27%.

Chlorpheniramine maleate can be used in the coating formula on the various pellet gum formulations. The following Table 7 shows some sugar and dextrose type formulas:

TABLE 7

(DRY WEIGHT PERCENT)

|  | EX. 42 | EX. 43 | EX. 44 | EX. 45 | EX. 46 | EX. 47 |
|---|---|---|---|---|---|---|
| SUGAR | 96.83 | 95.13 | 93.29 | 96.63 | 94.83 | 92.79 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |

TABLE 7-continued (DRY WEIGHT PERCENT)

| CHLORPHEN-IRAMINE MALEATE | 0.27 | 0.27 | 0.81[a] | 0.27 | 0.27 | 0.81[a] |
|---|---|---|---|---|---|---|

|  | EX. 48 | EX. 49 | EX. 50 | EX. 51 |
|---|---|---|---|---|
| DEXTROSE MONO-HYDRATE | 97.33 | 95.13 | 96.93 | 93.69 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| CHLORPHEN-IRAMINE MALEATE | 0.27 | 0.27 | 0.27 | 0.81[a] |

[a]All of the active agents is in the coating, which comprises 33% of the product.

The above formulations are made by making a syrup by dissolving the sugar and gum arabic in solution at about 75% solids at boiling, and suspending titanium dioxide or calcium carbonate in this syrup. Some of the dextrose may be added as a dry charge, which may also contain the active. Chlorpheniramine maleate may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Chlorpheniramine maleate may be dissolved in flavor and added to the coating. After the final coats are applied and dried, wax is applied to give a smooth polish.

Chlorpheniramine maleate may also be used in coating of sugarless gum centers. Like sugar gum centers, the base formulation can be increased in proportion to the amount of coating applied to the center. Formulations with and without chlorpheniramine maleate for low and high moisture gum can be used to make gum centers. Generally, the base level may be increased to 30–46% with the other ingredients proportionally reduced. Some typical gum formulas are in Table 8.

TABLE 8

(WEIGHT PERCENT)

|  | EX. 52 | EX. 53 | EX. 54 | EX. 55 | EX. 56 | EX. 57 | EX. 58 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 45.03 | 45.89 | 40.3 | 44.53 | 41.29 | 25.96 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| ACTIVE CHLORPHENIRAMINE MALEATE[b] | —[c] | 0.27 | 0.41 | —[c] | 0.27 | 0.41 | 0.54 |

[a]Lycasin brand hydrogenated starch hydrolyzate used instead of sorbitol liquid
[b]This material may be dissolved in water, glycerin, sorbitol liquid, or HSH.
[c]All of the active agent is in the coating, which comprises 33% of the product.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Chlorpheniramine maleate may be used in sugarless coatings with xylitol, sorbitol, maltitol, lactitol, hydrogenated isomaltulose and erythritol. The following table gives formulas for a xylitol coating:

TABLE 9

(DRY WEIGHT PERCENT)

|  | EX. 59 | EX. 60 | EX. 61 | EX. 62 | EX. 63 | EX. 64 |
|---|---|---|---|---|---|---|
| XYLITOL | 94.53 | 92.13 | 89.89 | 89.83 | 89.63 | 87.99 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| CHLORPHENIRAMINE MALEATE | 0.27 | 0.27 | 0.81[a)] | 0.27 | 0.27 | 0.81[a)] |

*Lake color dispersed in xylitol solution
**Calcium carbonate used in place of titanium dioxide
[a)] All of the active agent is in the coating, which comprises 33% of the product.

The above formulas are used to coat pellets by applying a xylitol/gum arabic solution in multiple coats and air drying. Color or whitener is also mixed in the solution. Chlorpheniramine maleate may be dissolved in water or flavor and added between coating applications or mixed with the hot syrup and used in the early stages of coating or used throughout the coating process. After pellets have been coated and dried, talc and wax are added to give a polish.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 10

(DRY WEIGHT PERCENT)

|  | EX. 65 | EX. 66 | EX. 67 | EX. 68 | EX. 69 | EX. 70 |
|---|---|---|---|---|---|---|
| MALTITOL | 96.53 | 94.63 | 91.29 | 86.53 | 75.83 | 68.69 |
| MALTITOL POWDER | — | — | — | 10.0 | 20.0 | 25.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| CHLORPHENIRAMINE MALEATE | 0.27 | 0.27 | 0.81[a)] | 0.27 | 0.27 | 0.81[a)] |

[a)] All of the active agent is in the coating, which comprises 33% of the product.

Maltitol, gum arabic, and whitener are blended into a syrup and applied to pellets. After all coating is applied and dried, talc and wax are added to give a polish. Chlorpheniramine maleate may be applied in a similar manner as in the previous xylitol coating, or may be preblended with the dry charge material.

In a similar manner, coatings with sorbitol, lactitol, and hydrogenated isomaltulose may be made in the coating formulas in Table 10 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, lactitol, erythritol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Some typical sugar type gum center formulations are shown in Table 11 containing pseudoephedrine hydrochloride, which is a nasal decongestant as an active medicament.

TABLE 11

(WEIGHT PERCENT)

|  | EX. 71 | EX. 72 | EX. 73 | EX. 74 | EX. 75 | EX. 76 |
|---|---|---|---|---|---|---|
| SUGAR | 52.0 | 48.0 | 46.5 | 44.0 | 40.0 | 37.5 |
| GUM BASE | 26.0 | 30.0 | 35.0 | 26.0 | 30.0 | 35.0 |
| CORN SYRUP | 20.0 | 19.0 | 15.00 | 18.0 | 17.0 | 14.00 |
| GLYCERIN | 1.0 | 1.0 | 1.00 | 1.0 | 1.0 | 1.00 |

TABLE 11-continued (WEIGHT PERCENT)

|  | EX. 71 | EX. 72 | EX. 73 | EX. 74 | EX. 75 | EX. 76 |
|---|---|---|---|---|---|---|
| PEPPERMINT FLAVOR | 1.0 | 1.0 | 1.00 | 1.0 | 1.0 | 1.00 |
| DEXTROSE MONOHYDRATE | — | — | — | 10.0 | 10.0 | 10.00 |
| ACTIVE PSEUDOEPHEDRINE HYDROCHLORIDE | —[a] | 1.0 | 1.5 | —[a] | 1.0 | 1.5 |

[a] All of the active agent is in the coating, which comprises 33% of the product.

Formulations with or without active pseudoephedrine hydrochloride can also be made similar to other formulations for low, medium, and high moisture formulas. Higher levels of base may be used with a corresponding decrease in other ingredients. Also, other sugars are polyols may be used in the gum center. Pseudoephedrine hydrochloride may be added to a gum center only, or to a gum coating with none in the center, or to both center and coating. Coated gum pieces are about 1.5 grams per piece, so to obtain 30 mg of pseudoephedrine hydrochloride in two gum pieces, total piece must contain 1.0%.

Pseudoephedrine hydrochloride can be used in the coating formula on the various pellet gum formulations. The following Table 12 shows some sugar and dextrose type formulas:

TABLE 12

(DRY WEIGHT PERCENT)

|  | EX. 77 | EX. 78 | EX. 79 | EX. 80 | EX. 81 | EX. 82 |
|---|---|---|---|---|---|---|
| SUGAR | 95.1 | 94.4 | 91.1 | 94.9 | 94.1 | 90.6 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| PSEUDOEPHEDRINE HYDROCHLORIDE | 2.0 | 1.0 | 3.0[a] | 2.0 | 1.0 | 3.0[a] |

|  | EX. 83 | EX. 84 | EX. 85 | EX. 86 |
|---|---|---|---|---|
| DEXTROSE MONOHYDRATE | 95.6 | 94.4 | 96.2 | 91.5 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| PSEUDOEPHEDRINE HYDROCHLORIDE | 2.0 | 1.0 | 1.0 | 3.0[a] |

[a] All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. Pseudoephedrine hydrochloride may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Pseudoephedrine hydrochloride may be dissolved in flavor and added to the coating. After the final coats are applied and dried, wax is applied to give a smooth polish.

As shown in Table 13, some of the sugar or dextrose may be added as a dry charge, which may also contain the active agent.

TABLE 13

(DRY WEIGHT PERCENT)

|  | EX. 87 | EX. 88 | EX. 89 | EX. 90 | EX. 91 | EX. 92 |
|---|---|---|---|---|---|---|
| SUGAR | 76.5 | 78.4 | — | — | 86.5 | — |
| DEXTROSE MONOHYDRATE | — | — | 76.5 | 83.3 | — | 84.1 |
| POWDER SUGAR* | 20.0 | 15.0 | — | — | — | — |
| POWDER DEXTROSE* | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| PSEUDOEPHEDRINE HYDROCHLORIDE | 1.0 | 3.0[a] | 1.0 | 3.0[a] | 1.0 | 3.0[a] |

*Powder and/or crystalline sugar may be used.

[a] All of the active agent is in the coating, which comprises 33% of the product.

In Examples 87–90 gum arabic powder is blended in the sugar syrup. In Examples 91 and 92, gum arabic powder is dry charged after a gum arabic solution is applied in the first stages of coating, then this is followed by a hard shell coating of-sugar solution or dextrose solution.

Pseudoephedrine hydrochloride may also be used in coating of sugarless gum centers. Like sugar gum centers, the base formulation can be increased in proportion to the amount of coating applied to the center. Formulations with and without pseudoephedrine hydrochloride similar to other formulations for low and high moisture gum can be used to make gum centers. Generally, the base level. may be increased to 30–46% with the other ingredients proportionally reduced. Some typical gum formulas are in Table 14.

TABLE 14

(WEIGHT PERCENT)

| | EX. 93 | EX. 94 | EX. 95 | EX. 96 | EX. 97 | EX. 98 | EX. 99 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.3 | 44.8 | 40.3 | 43.8 | 40.2 | 24.5 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| ACTIVE PSEUDOEPHEDRINE HYDROCHLORIDE[b] | —[c] | 1.0 | 1.5 | —[c] | 1.0 | 1.5 | 2.0 |

[a]Lycasin brand hydrogenated starch hydrolyzate used instead of sorbitol liquid
[b]This material may be dissolved in water, glycerin, sorbitol liquid, or HSH.
[c]All of the active agent is in the coating, which comprises 33% of the product.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, erythritol, xylitol, lactitol and hydrogenated isomaltulose may also be used in the gum center formulations. The texture may be adjusted by varying glycerin or sorbitol liquid. Sweetness of the center formulation can also be adjusted by varying the level of high intensity sweetener.

Pseudoephedrine hydrochloride may be used in sugarless coatings with xylitol, sorbitol, maltitol, lactitol, hydrogenated isomaltulose and erythritol. The following table gives formulas for a xylitol coating:

TABLE 15

(DRY WEIGHT PERCENT)

| | EX. 100 | EX. 101 | EX. 102 | EX. 103 | EX. 104 | EX. 105 |
|---|---|---|---|---|---|---|
| XYLITOL | 92.8 | 91.4 | 87.7 | 88.1 | 88.9 | 85.8 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| PSEUDOEPHEDRINE HYDROCHLORIDE | 2.0 | 1.0 | 3.0[a] | 2.0 | 1.0 | 3.0[a] |

*Lake color dispersed in xylitol solution
**Calcium carbonate used in place of titanium dioxide
[a]All of the active agent is in the coating, which comprises 33% of the product.

The above formulas are used to coat pellets by applying a xylitol/gum arabic solution in multiple coats and air drying. Color or whitener is also mixed in the solution. Pseudoephedrine hydrochloride may be dissolved in water or flavor and added between coating applications or mixed with the hot syrup and used in the early stages of coating or used throughout the coating process. After pellets have been coated and dried, talc and wax are added to give a polish.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 16

(DRY WEIGHT PERCENT)

| | EX. 106 | EX. 107 | EX. 108 | EX. 109 | EX. 110 | EX. 111 |
|---|---|---|---|---|---|---|
| MALTITOL | 94.8 | 93.9 | 89.1 | 84.8 | 75.1 | 66.5 |
| MALTITOL POWDER | — | — | — | 10.0 | 20.0 | 25.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| PSEUDOEPHEDRINE HYDROCHLORIDE | 2.0 | 1.0 | 3.0[a] | 2.0 | 1.0 | 3.0[a] |

[a]All of the active agent is in the coating, which comprises 33% of the product.

Maltitol powder is used to dry charge in the early stages of coating. Maltitol, gum arabic, and whitener are blended into a syrup and applied to pellets. After all coating is applied and dried, talc and wax are added to give a polish. Pseudoephedrine hydrochloride may be applied in a similar manner as in the previous xylitol coating examples, or may be preblended with the dry charge material.

In a similar manner, coatings with sorbitol, lactitol, and hydrogenated isomaltulose may be made in the coating formulas in Table 16 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, lactitol, erythritol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Liquid flavors generally are not added throughout the coating but at specific points throughout the process. When flavor is added, less air is used for drying until the flavor coating is covered by the next coatings and dried. Flavors may be various spearmint, peppermint, wintergreen, cinnamon, and fruit flavors to yield a wide variety of flavored chewing gum products.

Some typical sugar type gum center formulations are shown in Table 17 in which cetyl pyridimium chloride (CPC) can be added as the active medicament. This medicament can be used as an oral antimicrobial to reduce oral malodor and reduce oral bacteria. These formulas give a 1.5 gram piece containing 5 mg of CPC or 0.33%. Gum center formulas may or may not contain CPC, which has been encapsulated for controlled release.

TABLE 17

(WEIGHT PERCENT)

| | EX. 112 | EX. 113 | EX. 114 | EX. 115 | EX. 116 | EX. 117 |
|---|---|---|---|---|---|---|
| SUGAR | 52.0 | 48.67 | 47.5 | 44.0 | 40.67 | 38.5 |
| GUM BASE | 26.0 | 30.0 | 35.0 | 26.0 | 30.0 | 35.0 |
| CORN SYRUP | 20.0 | 19.0 | 15.0 | 18.0 | 17.0 | 14.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONO-HYDRATE | — | — | — | 10.0 | 10.0 | 10.0 |
| ACTIVE CPC | —[a] | 0.33 | 0.5 | —[a] | 0.33 | 0.5 |

[a] All of the active agent is in the coating, which comprises 33% of the product Formulations with or without CPC can also be made similar to other formulations for low, medium, and high moisture formulas. Higher levels of base may be used with a corresponding decrease in other ingredients. Also, other sugars and polyols may be used in the gum center. Cetyl pyridimium chloride may be added to a gum center only, into a gum coating with more in the center or to both center and coating.

CPC can be used in the coating formula on the various pellet gum formulations. The following Table 18 shows some sugar and dextrose type formulas:

TABLE 18

(DRY WEIGHT PERCENT)

| | EX. 118 | EX. 119 | EX. 120 | EX. 121 | EX. 122 | EX. 123 |
|---|---|---|---|---|---|---|
| SUGAR | 96.6 | 95.07 | 93.1 | 96.4 | 94.77 | 92.6 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| CPC | 0.5 | 0.33 | 1.0[a] | 0.5 | 0.33 | 1.0[a] |

TABLE 18-continued (DRY WEIGHT PERCENT)

| | EX. 124 | EX. 125 | EX. 126 | EX. 127 |
|---|---|---|---|---|
| DEXTROSE MONOHYDRATE | 97.1 | 95.07 | 96.87 | 93.5 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| CPC | 0.5 | 0.33 | 0.33 | 1.0[a] |

[a] All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. CPC may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. CPC may also be premixed with the flavor. After the final coats are applied and dried, wax is applied to give a smooth polish.

The above process gives a hard shell coating. Often a dry charge of powdered sugar or dextrose monohydrate may be used. This gives a somewhat softer coating. A dry charge may be used to build up a coating, but then finished with a straight syrup to obtain a hard shell. CPC may be added dry to the coating with the dry charge material. Table 19 gives these types of formulas.

TABLE 19

(DRY WEIGHT PERCENT)

| | EX. 128 | EX. 129 | EX. 130 | EX. 131 | EX. 132 | EX. 133 |
|---|---|---|---|---|---|---|
| SUGAR | 77.17 | 80.4 | — | — | 87.17 | — |
| DEXTROSE MONO-HYDRATE | — | — | 77.17 | 85.3 | — | 86.1 |
| POWDER SUGAR* | 20.0 | 15.0 | — | — | — | — |
| POWDER DEXTROSE* | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| CPC | 0.33 | 1.0[a] | 0.33 | 1.0[a] | 0.33 | 1.0[a] |

*Powder and/or crystalline sugar may be used.
[a] All of the active agent is in the coating, which comprises 33% of the product.

In Examples 128–131, gum arabic is blended in the sugar syrup. In Examples 132 and 133, gum arabic powder is dry charged after gum arabic solution is applied in the first stages of coating, then this is followed by a hard shell coating of sugar solution or dextrose solution.

Cetyl pyridimium chloride may also be used in coating of sugarless gum centers. Like sugar gum centers, the base formulation can be increased in proportion to the amount of coating applied to the center. Formulations with and without cetyl pyridimium chloride similar to other formulations for low and high moisture gum can be used to make gum centers. Generally, the base level may be increased to 30–46% with the other ingredients proportionally reduced. Some typical gum center formulas are in Table 20.

TABLE 20

(WEIGHT PERCENT)

| | EX. 134 | EX. 135 | EX. 136 | EX. 137 | EX. 138 | EX. 139 | EX. 140 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.97 | 45.8 | 40.3 | 44.47 | 41.2 | 25.84 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a)] | 10.0[a)] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| CPC[b)] | —[c)] | 0.33 | 0.5 | —[c)] | 0.33 | 0.5 | 0.66 |

[a)]Lycasin brand hydrogenated starch hydrolyzate used instead of sorbitol liquid.
[b)]This material may be dissolved in water, glycerin, sorbitol liquid, or HSH.
[c)]All of the active agent is in the coating, which comprises 33% of the product.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Cetyl pyridimium chloride may be used in sugarless coatings with xylitol, sorbitol, maltitol, lactitol, hydrogenated isomaltulose and erythritol. The following table gives formulas for a xylitol coating:

TABLE 21

(DRY WEIGHT PERCENT)

| | EX. 141 | EX. 142 | EX. 143 | EX. 144 | EX. 145 | EX. 146 |
|---|---|---|---|---|---|---|
| XYLITOL | 94.3 | 92.07 | 89.7 | 89.6 | 89.57 | 87.8 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| CPC | 0.5 | 0.33 | 1.0[a)] | 0.5 | 0.33 | 1.0[a)] |

*Lake color dispersed in xylitol solution
**Calcium carbonate used in place of titanium dioxide
[a)]All of the active agent is in the coating, which comprises 33% of the product.

The above formulas are used to coat pellets by applying a xylitol/gum arabic solution in multiple coats and air drying. Color or whitener is also mixed in the solution. CPC may be dissolved in water or flavor and added between coating applications, or mixed with the hot syrup and used in the early stages of coating or used throughout the coating process. CPC may also be blended with the flavor used for coating. After pellets have been coated and dried, talc and wax are added to give a polish.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made. However, it may be preferable to add a dry charge to quicken the drying process before the pellets get too sticky. The following formulations may be used.

TABLE 22

(DRY WEIGHT PERCENT)

| | EX. 147 | EX. 148 | EX. 149 | EX. 150 | EX. 151 | EX. 152 |
|---|---|---|---|---|---|---|
| MALTITOL | 96.3 | 94.57 | 91.1 | 86.3 | 75.77 | 68.5 |
| MALTITOL POWDER | — | — | — | 10.0 | 20.0 | 25.0 |
| ARABINO-GALACTAN | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| CETYL PYRIDIMIUM CHLORIDE | 0.5 | 0.33 | 1.0[a)] | 0.5 | 0.33 | 1.0[a)] |

[a)]All of the active agent is in the coating, which comprises 33% of the product.

Maltitol powder is used to dry charge in the early stages of coating. Maltitol, gum arabic, and whitener are blended into a syrup and applied to pellets. After all coating is applied and dried, talc and wax are added to give a polish. Cetyl pyridimium chloride may be applied in a similar manner as in the previous xylitol coating examples, or preblended with the dry charge materials.

In a similar manner, coatings with sorbitol, lactitol, and hydrogenated isomaltulose may be made in the coating formulas in Table 22 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, erythritol, lactitol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Liquid flavors generally are not added throughout the coating but at specific points throughout the process. When flavor is added, less air is used for drying until the flavor coating is covered by the next coatings and dried. Flavors may be various spearmint, peppermint, wintergreen, cinnamon, and fruit flavors to yield a wide variety of flavored chewing gum products.

Some typical sugar type gum center formulations are shown in Table 23, in which ketoprofen can be added as the active medicament. Ketoprofen is an analgesic to reduce inflammation and pain. These formulas give a 1.5 gram piece containing 12.5 mg of ketoprofen or 0.83% of the total gum product. Gum center formulas may or may not contain encapsulated or controlled release ketoprofen.

TABLE 23

(WEIGHT PERCENT)

| | EX. 153 | EX. 154 | EX. 155 | EX. 156 | EX. 157 | EX. 158 |
|---|---|---|---|---|---|---|
| SUGAR | 52.0 | 48.17 | 46.75 | 44.0 | 40.17 | 37.75 |
| GUM BASE | 26.0 | 30.0 | 35.0 | 26.0 | 30.0 | 35.0 |
| CORN SYRUP | 20.0 | 19.0 | 15.0 | 18.0 | 17.0 | 14.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONO-HYDRATE | — | — | — | 10.0 | 10.0 | 10.0 |
| KETO-PROFEN | —[a] | 0.83 | 1.25 | —[a] | 0.83 | 1.25 |

[a] All of the active agent is in the coating, which comprises 33% of the product Formulations with or without ketoprofen can also be made similar to other formulations for low, medium, and high moisture formulas. Higher levels of base may be used with a corresponding decrease in other ingredients. Also, other sugars and polyols may be used in the gum center. Ketoprofen may be added to a gum center only, into a gum coating with none in the center, or to both center and coating.

Ketoprofen can be used in the coating formula on the various pellet gum formulations. The following Table 24 shows some sugar and dextrose type formulas:

TABLE 24

(DRY WEIGHT PERCENT)

| | EX. 159 | EX. 160 | EX. 161 | EX. 162 | EX. 163 | EX. 164 |
|---|---|---|---|---|---|---|
| SUGAR | 96.1 | 94.57 | 91.6 | 95.9 | 94.27 | 91.1 |
| GUM ARABIC | 2.0 | 3.0 | 4.0 | 2.0 | 3.0 | 4.0 |
| TITANIUM DIOXIDE | 0.5 | 1.0 | 1.0 | — | — | — |

TABLE 24-continued (DRY WEIGHT PERCENT)

| | EX. 159 | EX. 160 | EX. 161 | EX. 162 | EX. 163 | EX. 164 |
|---|---|---|---|---|---|---|
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |
| KETO-PROFEN | 1.0 | 0.83 | 2.5[a] | 1.0 | 0.83 | 2.5[a] |

| | EX. 165 | EX. 166 | EX. 167 | EX. 168 |
|---|---|---|---|---|
| DEXTROSE MONOHYDRATE | 96.6 | 94.57 | 96.37 | 92.0 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| KETOPROFEN | 1.0 | 0.83 | 0.83 | 2.5[a] |

[a] All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. Ketoprofen may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Ketoprofen may also be premixed with the flavor. After the final coats are applied and dried, wax is applied to give a smooth polish.

The above process gives a hard shell coating. Often a dry charge of powdered sugar or dextrose monohydrate may be used. This gives a somewhat softer coating. A dry charge, which also may contain the active, may be used to build up a coating, but then finished with a straight syrup to obtain a hard shell. Table 25 gives these types of formulas.

TABLE 25

(DRY WEIGHT PERCENT)

| | EX. 169 | EX. 170 | EX. 171 | EX. 172 | EX. 173 | EX. 174 |
|---|---|---|---|---|---|---|
| SUGAR | 76.67 | 78.9 | — | — | 86.67 | — |
| DEXTROSE MONO-HYDRATE | — | — | 76.67 | 83.8 | — | 84.6 |
| POWDER SUGAR* | 20.0 | 15.0 | — | — | — | — |
| POWDER DEXTROSE* | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| KETO-PROFEN | 0.83 | 2.5[a] | 0.83 | 2.5[a] | 0.83 | 2.5[a] |

*Powder and/or crystalline sugar may be used.
[a] All of the active agent is in the coating, which comprises 33% of the product.

In Examples 169–172, gum arabic is blended in the sugar syrup. In Examples 173 and 174, gum arabic powder is dry charged after gum arabic solution is applied in the first stages of coating, then this is followed by a hard shell coating of sugar solution or dextrose solution.

Ketoprofen may also be used in coating of sugarless gum centers. Like sugar gum centers, the base formulation can be increased in proportion to the amount of coating applied to the center. Formulations with and without ketoprofen for low and high moisture gum can be used to make gum centers. Generally, the base level may be increased to 30–46% with the other ingredients proportionally reduced. Some typical gum formulas are in Table 26.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made.

TABLE 26

(WEIGHT PERCENT)

|  | EX. 175 | EX. 176 | EX. 177 | EX. 178 | EX. 179 | EX. 180 | EX. 181 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.47 | 45.05 | 40.3 | 43.97 | 40.45 | 24.83 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0$^{a)}$ | 10.0$^{a)}$ |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| KETOPROFEN$^{b)}$ | —$^{c)}$ | 0.83 | 1.25 | —$^{c)}$ | 0.83 | 1.25 | 1.67 |

$^{a)}$Lycasin brand hydrogenated starch hydrolyzate used instead of sorbitol liquid.
$^{b)}$Ketoprofen may be dissolved in water, glycerin, sorbitol liquid, HSH, or flavor.
$^{c)}$All of the active agent is in the coating, which comprises 33% of the product.

In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Ketoprofen may be used in sugarless coatings with xylitol, sorbitol, maltitol, lactitol, hydrogenated isomaltulose and erythritol. The following table gives formulas for a xylitol coating:

TABLE 27

(DRY WEIGHT PERCENT)

|  | EX. 182 | EX. 183 | EX. 184 | EX. 185 | EX. 186 | EX. 187 |
|---|---|---|---|---|---|---|
| XYLITOL | 93.8 | 91.57 | 88.2 | 89.1 | 89.07 | 86.3 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| KETOPROFEN | 1.0 | 0.83 | 2.5$^{a)}$ | 1.0 | 0.83 | 2.5$^{a)}$ |

*Lake color dispersed in xylitol solution.
**Calcium carbonate used in place of titanium dioxide.
$^{a)}$All of the active agent is in the coating, which comprises 33% of the product.

The above formulas are used to coat pellets by applying a xylitol/gum arabic solution in multiple coats and air drying. Color or whitener is also mixed in the solution. After pellets have been coated and dried, talc and wax are added to give a polish. Ketoprofen may be dissolved in water or flavor and added between coating applications, or mixed with the hot syrup and used in the early stages of coating or used throughout the coating process.

However, it may be preferable to add a dry charge to quicken the drying process before the pellets get too sticky. The following formulations may be used.

TABLE 28

(DRY WEIGHT PERCENT)

|  | EX. 188 | EX. 189 | EX. 190 | EX. 191 | EX. 192 | EX. 193 |
|---|---|---|---|---|---|---|
| MALTITOL | 95.8 | 94.07 | 89.6 | 85.8 | 75.27 | 67.0 |
| MALTITOL POWDER | — | — | — | 10.0 | 20.0 | 25.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| KETOPROFEN | 1.0 | 0.83 | 2.5$^{a)}$ | 1.0 | 0.83 | 2.5$^{a)}$ |

$^{a)}$All of the active agent is in the coating, which comprises 33% of the product.

Maltitol powder is used to dry charge in the early stages of coating. Maltitol, gum arabic, and whitener are blended into a syrup and applied to pellets. After all coating is applied and dried, talc and wax are added to give a polish. Ketoprofen may be applied in a similar manner as in the previous xylitol coating examples, or preblended with the dry charge material and added to the coating.

In a similar manner, coatings with sorbitol, lactitol, and hydrogenated isomaltulose may be made in the coating formulas in Table 28 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, erythritol, lactitol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Some typical sugar type gum center formulations are shown in Table 29 in which dextromethorphan hydrobromide can be added as the active medicament. This material is an antitussive for cough relief. These formulas give a 1.5 gram piece containing 15 mg of dextromethorphan hydrobromide or 1.0% of gum product. Gum centers may or may not contain dextromethorphan hydrobromide.

TABLE 29

(WEIGHT PERCENT)

| | EX. 194 | EX. 195 | EX. 196 | EX. 197 | EX. 198 | EX. 199 |
|---|---|---|---|---|---|---|
| SUGAR | 52.0 | 48.0 | 46.5 | 44.0 | 40.0 | 37.5 |
| GUM BASE | 26.0 | 30.0 | 35.0 | 26.0 | 30.0 | 35.0 |
| CORN SYRUP | 20.0 | 19.0 | 15.0 | 18.0 | 17.0 | 14.0 |
| GLYCERIN | 1.0 | 1.0 | 1.0 | 1.0 | 1.0 | 1.0 |
| PEPPERMINT FLAVOR | 1.0 | 1.0 | 1.0 | 1.0 | 1.0 | 1.0 |
| DEXTROSE MONO-HYDRATE | — | — | — | 10.0 | 10.0 | 10.0 |
| DEXTRO-METHOR-PHAN HBr | —[a] | 1.0 | 1.5 | —[a] | 1.0 | 1.5 |

[a]All of the active agent is in the coating, which comprises 33% of the product.

Formulations with or without dextromethorphan hydrobromide can also be made for low, medium, and high moisture formulas. Higher levels of base may be used with a corresponding decrease in other ingredients. Also, other sugars and polyols may be used in the gum center. Dextromethorphan hydrobromide may be added to the gum center only, into a gum coating with none in the center, or both center and coating.

Dextromethorphan hydrobromide can then be used in the coating formula on the various pellet gum formulations. The following Table 30 shows some sugar and dextrose type formulas:

TABLE 30

(DRY WEIGHT PERCENT)

| | EX. 200 | EX. 201 | EX. 202 | EX. 203 | EX. 204 | EX. 205 |
|---|---|---|---|---|---|---|
| SUGAR | 95.1 | 94.4 | 91.1 | 94.9 | 94.1 | 90.6 |
| GUM ARABIC | 2.0 | 3.0 | 4.0 | 2.0 | 3.0 | 4.0 |
| TITANIUM DIOXIDE | 0.5 | 1.0 | 1.0 | — | — | — |
| CALCIUM CARBONATE | — | — | — | 0.5 | 1.0 | 2.0 |
| FLAVOR | 0.3 | 0.5 | 0.8 | 0.5 | 0.8 | 0.3 |
| WAX | 0.1 | 0.1 | 0.1 | 0.1 | 0.1 | 0.1 |

TABLE 30-continued (DRY WEIGHT PERCENT)

| | | | | | | |
|---|---|---|---|---|---|---|
| DEXTRO-METHOR-PHAN HBr | 2.0 | 1.0 | 3.0[a] | 2.0 | 1.0 | 3.0[a] |

| | EX. 206 | EX. 207 | EX. 208 | EX. 209 |
|---|---|---|---|---|
| DEXTROSE MONOHYDRATE | 95.6 | 94.4 | 96.2 | 91.5 |
| GUM ARABIC | 1.5 | 3.0 | 1.5 | 3.0 |
| TITANIUM DIOXIDE | 0.5 | 1.0 | — | — |
| CALCIUM CARBONATE | — | — | 1.0 | 2.0 |
| FLAVOR | 0.3 | 0.5 | 0.2 | 0.4 |
| WAX | 0.1 | 0.1 | 0.1 | 0.1 |
| DEXTRO-METHORPHAN HBr | 2.0 | 1.0 | 1.0 | 3.0[a] |

[a]All of the active agent is in the coating, which comprises 33% of the product.

The above formulations are made by making a syrup by dissolving the sugar and gum arabic in solution at about 75% solids at boiling, and suspending titanium dioxide or calcium carbonate in this syrup. Dextromethorphan hydrobromide may be dissolved in water, not mixed with hot syrup, but applied between coatings, or it may be added to the hot syrup and used in the early stages of coating or used throughout the coating process. Flavor is not mixed with the hot syrup, but added at low levels with one or more coats. Dextromethorphan HBr may also be premixed with the flavor. After the final coats are applied and dried, wax is applied to give a smooth polish.

The above process gives a hard shell coating. Often a dry charge of powdered sugar or dextrose monohydrate may be used. This gives a somewhat softer coating. A dry charge may be used to build up a coating, but then finished with a straight syrup to obtain a hard shell. Dextromethorphan hydrobromide may also be added to the dry charge material. Table 31 gives these types of formulas.

TABLE 31

(DRY WEIGHT PERCENT)

| | EX. 210 | EX. 211 | EX. 212 | EX. 213 | EX. 214 | EX. 215 |
|---|---|---|---|---|---|---|
| SUGAR | 76.5 | 78.4 | — | — | 86.5 | — |
| DEXTROSE MONO-HYDRATE | — | — | 76.5 | 83.3 | — | 84.1 |
| POWDER SUGAR* | 20.0 | 15.0 | — | — | — | — |
| POWDER DEXTROSE* | — | — | 20.0 | 10.0 | — | — |
| GUM ARABIC POWDER | 2.0 | 3.0 | 2.0 | 3.0 | 8.0 | 8.0 |
| GUM ARABIC SOLUTION | — | — | — | — | 4.0 | 4.0 |
| FLAVOR | 0.4 | 0.5 | 0.4 | 0.6 | 0.4 | 0.8 |
| WAX | 0.1 | 0.1 | 0.1 | 0.1 | 0.1 | 0.1 |
| DEXTRO-METHOR-PHAN HBr | 1.0 | 3.0[a] | 1.0 | 3.0[a] | 1.0 | 3.0[a] |

*Powder and/or crystalline sugar may be used.
[a]All of the active agent is in the coating, which comprises 33% of the product.

In Examples 210–213 gum arabic is blended in the sugar syrup. In Examples 214 and 215, gum arabic powder is dry charged after a gum arabic solution is applied in the first stages of coating, then this is followed by a hard shell coating of sugar solution or dextrose solution.

Dextromethorphan hydrobromide may also be used in coating of sugarless gum centers. Like sugar gum centers, the base formulation can be increased in proportion to the amount of coating applied to the center. Formulations with and without dextromethorphan hydrobromide for low and high moisture gum can be used to make gum centers. Generally, the base level may be increased to 30–46% with the other ingredients proportionally reduced. Some typical gum center formulas are in Table 32.

Color or whitener is also mixed in the solution. After pellets have been coated and dried, talc and wax are added to give a polish. Dextromethorphan hydrobromide may be dissolved in water or flavor and added between coating applications, or mixed with hot syrup and used in the early stages of coating or used throughout the coating process.

For coating formulas based on sorbitol, maltitol, lactitol, erythritol, and hydrogenated isomaltulose, gum arabic can be used as a binder and film former, and a crystallization modifier to help facilitate coating. Generally these polyols are more difficult to coat using only a straight syrup, but with proper technique a good smooth hard shell can be made.

TABLE 32

(WEIGHT PERCENT)

| | EX. 216 | EX. 217 | EX. 218 | EX. 219 | EX. 220 | EX. 221 | EX. 222 |
|---|---|---|---|---|---|---|---|
| GUM BASE | 35.0 | 35.0 | 30.0 | 30.0 | 30.0 | 40.0 | 50.0 |
| CALCIUM CARBONATE | — | — | 5.0 | 10.0 | 15.0 | — | — |
| SORBITOL | 43.3 | 44.3 | 43.3 | 40.3 | 43.8 | 38.7 | 24.5 |
| MANNITOL | 10.0 | 10.0 | 5.0 | 10.0 | — | 8.0 | 10.0 |
| GLYCERIN | — | 8.0 | 2.0 | — | 8.0 | 2.0 | 2.0 |
| SORBITOL LIQUID | 10.0 | — | 10.0 | 8.0 | — | 6.0[a] | 10.0[a] |
| FLAVOR | 1.5 | 1.5 | 1.5 | 1.5 | 2.0 | 2.0 | 1.3 |
| HIGH INTENSITY SWEETENER | 0.2 | 0.2 | 0.2 | 0.2 | 0.2 | 0.3 | 0.2 |
| DEXTROMETHORPHAN HBr[b] | —[c] | 1.0 | 3.0 | —[c] | 1.0 | 3.0 | 2.0 |

[a]Lycasin brand hydrogenated starch hydrolyzate used instead of sorbitol liquid
[b]Dextromethorphan HBr may be dissolved in water, glycerin, sorbitol liquid, HSH, or flavor
[c]All of the active agent is in the coating, which comprises 33% of the product In the above center formulations, the high intensity sweetener used is aspartame. However other high intensity such as alitame, acesulfame K, salts of acesulfame, cyclamate and its salts, saccharin and its salts, neotame, sucralose, thaumatin, monellin, dihydrochalcone, stevioside, glycyrrhizin and combinations thereof may be used in any of the examples with the level adjusted for sweetness.

Lycasin and other polyols such as maltitol, xylitol, erythritol, lactitol and hydrogenated isomaltulose may also be used in the gum center formulations at various levels. The texture may be adjusted by varying glycerin or sorbitol liquid. Sweetness of the center formulation can also be adjusted by varying the level of high intensity sweetener.

Dextromethorphan hydrobromide may be used in sugarless coatings with xylitol, sorbitol, maltitol, lactitol, hydrogenated isomaltulose and erythritol. The following table gives formulas for a xylitol coating:

TABLE 33

(DRY WEIGHT PERCENT)

| | EX. 223 | EX. 224 | EX. 225 | EX. 226 | EX. 227 | EX. 228 |
|---|---|---|---|---|---|---|
| XYLITOL | 92.8 | 91.4 | 87.7 | 88.1 | 88.9 | 85.8 |
| GUM ARABIC | 4.0 | 6.0 | 7.0 | 8.5 | 8.5 | 10.0 |
| FLAVOR | 0.5 | 0.5 | 0.7 | 0.7 | 0.9 | 0.5 |
| TITANIUM DIOXIDE | 0.5 | 0.9 | — | 0.5 | 0.5** | 0.5** |
| TALC | 0.1 | 0.1 | 0.1 | 0.1 | 0.1 | 0.1 |
| WAX | 0.1 | 0.1 | 0.1 | 0.1 | 0.1 | 0.1 |
| COLOR* | — | — | 1.4 | — | — | — |
| DEXTROMETHORPHAN HBr | 2.0 | 1.0 | 3.0[a] | 2.0 | 1.0 | 3.0[a] |

*Lake color dispersed in xylitol solution
**Calcium carbonate used in place of titanium dioxide
[a]All of the active agent is in the coating, which comprises 33% of the product The above formulas are used to coat pellets by applying a xylitol/gum arabic solution in multiple coats and air drying. However, it may be preferable to add a dry charge to quicken the drying process before the pellets get too sticky. The active may be premixed with the dry charge material. The following formulations may be used.

TABLE 34

(DRY WEIGHT PERCENT)

| | EX. 229 | EX. 230 | EX. 231 | EX. 232 | EX. 233 | EX. 234 |
|---|---|---|---|---|---|---|
| MALTITOL | 94.8 | 93.9 | 87.1 | 91.8 | 85.1 | 76.5 |
| MALTITOL POWDER | — | — | — | 5.0 | 10.0 | 15.0 |
| GUM ARABIC | 2.0 | 4.0 | 6.0 | 2.0 | 3.0 | 4.0 |
| FLAVOR | 0.5 | 0.4 | 0.7 | 0.5 | 0.3 | 0.7 |
| TITANIUM DIOXIDE | 0.5 | 0.5 | 1.0 | 0.5 | 0.4 | 0.6 |
| TALC | 0.1 | 0.1 | 0.1 | 0.1 | 0.1 | 0.1 |
| WAX | 0.1 | 0.1 | 0.1 | 0.1 | 0.1 | 0.1 |
| DEXTROMETHORPHAN HBr | 2.0 | 1.0 | 3.0[a] | 2.0 | 1.0 | 3.0[a] |

[a]All of the active agent is in the coating, which comprises 33% of the product.

Maltitol powder is used to dry charge in the early stages of coating. Maltitol, gum arabic, and whitener is blended into a syrup and applied to pellets. After all coating is applied and dried, talc and wax are added to give a polish. Dextromethorphan may be applied in a similar manner as the previous xylitol examples, or added with the dry charge material.

In a similar manner, coatings with sorbitol, lactitol, and hydrogenated isomaltulose may be made in the coating formulas in Table 34 by replacing maltitol with any one of the other polyols and maltitol powder with the polyol powder. Like maltitol, the other polyols may become sticky during the coating and drying process, so the dry powder charge may be needed to give the proper drying. In the later stages of the coating process, less gum arabic could be used and a more pure polyol syrup could be used to give a smooth surface. Also, the dry charge would only be used in the early stages of the coating process.

In addition to dry charging with the specific polyol, other ingredients may be added to the dry charge to help absorb moisture. These materials could be inert such as talc, calcium carbonate, magnesium carbonate, starches, gums like arabinogalactan, gum talha, gum arabic or other moisture absorbing materials. Also, powdered sweeteners or flavors could be added with the dry charge.

Some polyols such as sorbitol, maltitol, erythritol, lactitol, or hydrogenated isomaltulose are not sufficiently sweet compared to sugar or xylitol, so high intensity sweeteners may be added to the coating, such as aspartame, acesulfame K, salts of acesulfame, cyclamate and its salts, saccharin and its salts, alitame, sucralose, thaumatin, monellin, dihydrochalcone, glycyrrhizin, neotame, and combinations thereof. If a hot syrup is applied, heat may degrade the sweetener so only stable sweeteners should be used. Generally high intensity sweeteners are added with the polyol/gum arabic solution to obtain an even distribution in the coatings.

Liquid flavors generally are not added throughout the coating but at specific points throughout the process. When flavor is added, less air is used for drying until the flavor coating is covered by the next coatings and dried. Flavors may be various spearmint, peppermint, wintergreen, cinnamon, and fruit flavors to yield a wide variety of flavored chewing gum products.

The following gum center formulation was made as a gum pellet center and coated with the gum coating formulation and procedure:

Example 235

| Gum Center | % | |
|---|---|---|
| Gum Base | 47.0 | |
| Sorbitol | 39.52 | |
| Liquid Sorbitol | 7.5 | |
| Flavors | 2.36 | |
| Encapsulated Flavors | 2.0 | |
| Glycerin | 0.75 | |
| Encapsulated Sweeteners | 0.87 | |
| | 100.0 | |
| Gum Coating | Coating Syrup 1.% | Coating Syrup 2.% |
| Xylitol | 63.03 | 74.35 |
| Water | 11.14 | 13.15 |
| 40% Gum Tahla solution | 20.87 | 7.96 |
| Titanium Dioxide whitener | 0.37 | 0.44 |
| Peppermint Flavor* | 0.81 | 0.0 |
| Caffeine | 3.78 | 4.10 |
| | 100.0 | 100.0 |

*Flavor added in 2 additions after 10th and 15th coat within coating syrup 1.

Initial center piece weight was 0.956 grams. Gum was coated to a finished piece weight of 1.46 grams to give a 34.5% coating. Coating syrup 1 was used to coat the first 60% of the coating to a piece weight of 1.26 grams. Coating syrup 2 was used to coat to the final piece weight. Individual piece analysis of 5 pieces yielded a level of 26.1 mg of caffeine per piece. For a 2 piece dosage, caffeine level is 52.2 mg.

This gum product was used in a caffeine absorption study to compare release and absorption uptake of caffeine from gum and beverages. The test results showed that gum is a faster delivery vehicle for caffeine when compared to the same level in beverages as measured by blood plasma caffeine. Caffeine was taken up faster in the test subject's plasma after delivery via gum than after delivery of same caffeine dose via coffee, cola and tea.

Comparisons of caffeine delivery between chewing gum and the three beverages are demonstrated by statistically significant differences in one or more of the following parameters:

1. Plasma caffeine concentration is significantly greater for gum vs. beverages within the first 10 to 30 minutes after caffeine delivery. This correlates to faster uptake.
2. Plasma absorption rate constant (A-rate) larger for gum vs. one or more beverages (2). Plasma absorption half life (abs. half-life) smaller for gum vs. one or more beverages (2). Time of peak caffeine plasma concentration (T-max) smaller for gum than one or more of the beverages (2).

A clinical trial study was performed where six subjects participated in the test, blood was drawn and plasma separated. Blood sampling occurred prior to, and at preset time intervals following a caffeine level of 50–55 mg released through the test delivery vehicle. Five different studies were completed: gum (with saliva swallowed, G2), gum (with saliva expectorated, G3), coffee (ingested COF), cola (ingested COK) and tea (ingested T). Blood samples of 5 ml were collected and the plasma portion separated, stored, and extracted and analyzed. A method was developed for the extraction and analysis of caffeine in fluids, which reports results as the concentration of caffeine in the plasma.

Data from the six subjects participating in the study were compiled, analyzed, and graphed, with mean plasma caffeine concentrations at specific time intervals determined. Analysis of variance (ANOVA) were performed on the means to determine statistical significance.

Pharmacokinetic parameters were determined through Wagner's 1967 Method of Residuals using a pharmacokinetic software package. Absorption rate constants and absorption half-life were also determined through the analysis of the absorption phase of the plots by linear regression since the absorption phase followed zero order kinetics.

The conclusions were as follows:
1. There was a faster uptake of caffeine in plasma during the early time intervals post dose 10 minutes to 25 minutes (T10–T25) via gum delivery vs. the same level of caffeine delivered via coffee and cola. For example, the average level of plasma caffeine (at T=10 minutes) present after gum chew is 0.545 $\mu$g/ml compared to 0.186 $\mu$g/ml for coffee and 0.236 $\mu$g/ml for cola. In other words, with the same level of caffeine being delivered from the three different vehicles, at T10 there is 3 times more caffeine present in plasma after chewing gum than from ingesting coffee and 2 times more caffeine from gum than from cola. The results of the tea study proved to be too variable due to instrument problems and repeat freeze/thawing of the samples. They were not included in the calculations.
2. Classical pharmacokinetic parameters, T-max, A-rate constant, abs. half-life, do not tell the story of faster uptake in the time interval of interest (T10–T25) in this study. This is due in part to the calculation using the Method of Residuals. This method was derived using classical pharmacokinetic curves which do not have much fluctuation in the data in that the drug concentration (usually measured every hour) increases to a sharp T-max, then decreases, without any fluctuation. In comparison, the data did contain minor fluctuations, due most likely to a combination of factors: measurement of plasma concentrations every five minutes rather than every quarter hour to one hours, caffeine binding with plasma protein, combination of both sublingual and gut absorption being detected. The plasma caffeine concentration followed the same trends as in classical pharmacokinetic curves, except that the concentration increased to a broad T-max, then decreased, and some of the points in the curve fluctuated up and down.

A-rate constant and abs. half-life determinations were also made through linear regression. No significant differences were noted in the means, though a trend was noted: the A-rate for the gum study (G2) was greater than that for coffee and cola for subjects 1–4 and the abs. half-life for the G2 study was less than that for coffee and cola for subjects 1–4. For example, the G2 abs. half-life averaged 13±4 minutes for subjects 1–4, 28±2 minutes for subjects 5 and 6, indicating faster absorption for subjects 1–4. This is due to the different rates of sublingual absorption between the subjects. The amount of caffeine absorbed sublingually was 21±7 mg for subjects 1–4, and 10±1 mg for subjects 5 and 6, accounting for the increased A-rate and decreased abs. half-life in subjects 1–4. An ANOVA separating subjects 1–4 from 5 and 6 indicated that for subjects 1–4 cola abs. half-life is statistically greater than G2 abs. half-life (p=0.10), and the G2 A-rate is statistically greater than both the cola and coffee A-rate (p=0.05).

3. It was shown that significant levels of caffeine are absorbed sublingually directly into the bloodstream via delivery from gum This was demonstrated through the testing of caffeinated gum where the saliva was expectorated. Even though the saliva was expectorated, 20–50% of the caffeine was absorbed through the oral cavity. This accounts for the early uptake into the bloodstream.

Example 236

| Gum Center | % |
| --- | --- |
| Gum Base | 33.0 |
| Calcium Carbonate | 13.0 |
| Sorbitol | 44.23 |
| Glycerin | 4.0 |
| Flavors | 2.32 |
| Encapsulated Caffeine* | 1.5 |
| Free Caffeine | 0.45 |
| Lecithin | 0.6 |
| Encapsulated Sweeteners | 0.9 |
| | 100.0 |

| Gum Coating (dry) | Coating Syrup 3% | Coating Syrup 4% |
| --- | --- | --- |
| Xylitol | 64.14 | 76.23 |
| Water | 11.14 | 13.15 |
| 40% Gum Tahla solution | 20.87 | 7.96 |
| Titanium Dioxide whitener | 0.4 | 0.4 |
| Peppermint Flavor** | 1.4 | 0.0 |
| Sweeteners | 0.27 | 0.27 |
| Carnauba Wax/Talc polishing agents | 0.0 | 0.27*** |
| Caffeine | 1.78 | 1.72 |
| | 100.0 | 100.0 |

*Spray dried maltodextrin/caffeine at 50% active caffeine.
**Flavor added in 3 additions after 3 separate syrup addition within coating syrup 1.
***Polished after completion of coating.

Initial center piece weight was 0.995 grams. Gum was coated to a finished piece weight of 1.52 grams to give a 34.5% coating. Coating syrup 3 was used to coat the first 60% of the coating to a piece weight of 1.30 grams. Coating syrup 4 was used to coat to the final piece weight. Individual piece analysis of 5 pieces yielded a level of 20.0±0.8 mg of caffeine per piece. For a two piece dosage, caffeine level is 40.0 mg.

This gum product was used in a caffeine absorption study to compare release and absorption uptake of caffeine from gum verses pills. The test results showed that gum is a faster delivery vehicle for caffeine when compared to a similar level in a pill as measured by blood plasma caffeine. Caffeine was taken up faster in the test subject's plasma after deliver, via gum than after delivery of same caffeine dose via a pill.

Data from the six subjects participating in each study were compiled, analyzed, and graphed, with mean plasma caffeine concentrations at specific time intervals determined. Analysis of variance (ANOVA) and Student t-Tests were performed on the means to determine statistical significance. Pharmacokinetic parameters were done using a pharmacokinetic software package. The gums tested were pellet Example 235, containing all the caffeine in the coating and delivering approximately 50 mg caffeine after chewing two pellets (designated as G2, G4, or 50 mg pellet), and Example 236, containing caffeine in the coating and center, and delivering approximately 40 mg caffeine after chewing two pellets (designated G5 or 40 mg pellet). Both pellets were compared to Pro-Plus™ pill, containing approximately 50 mg caffeine in one pill (designated as Pill 1, Pill 2, or 50 mg pill). Pro-Plus™ 50 mg tablet is manufactured by the product license holder: PP Products, 40 Broadwater Road, Welayn Garden City, Harts, AL7 Bay, UK. Caffeine analysis were analyzed at 48.3 mg±1.4 mg caffeine per pill (avg. of n=5).

It was concluded that caffeine uptake in the bloodstream was faster for gum than a pill, based on the following:

1. Faster uptake of plasma caffeine via gum delivery was found during the early time intervals post dose 5 minutes to 50 minutes (T5–T50) when compared to the same level of caffeine delivered via a pill (50 mg). For example, with the same level of caffeine being delivered from the two different vehicles, on average, at T5 there is 30 times more caffeine detected in plasma after chewing gum (0.205 $\mu$g/ml) than after ingesting a pill (0.006 $\mu$g/ml). At T10 there is 16 times more caffeine detected in plasma after chewing gum (0.546 $\mu$g/ml) than after ingesting a pill (0.034 $\mu$g/ml). Average plasma caffeine levels significantly greater than the pill at a=0.01 for T5, and a=0.005 for T10.

2. Classical pharmacokinetic parameters, T-Max (time for peak plasma caffeine concentration) and Abs. ½ Life (absorbance ½ life, time for caffeine concentration to be ½ of peak) were significantly different for caffeine delivered via 50 mg pellet gum (Example 235) than via a 50 mg pill. Faster uptake of plasma caffeine was demonstrated via delivery from gum compared to a pill due to the average plasma Abs. ½ Life and average plasma T-Max being significantly smaller for gum than the pill. For the 50 mg pellet gum, the average Abs. ½ Life=12.84 min and the average T-Max–36.5 min. compared to the 50 mg pill with an average Abs. ½ Life=24.47 min (pill significantly greater than gum, a=0.0075, and an average T-Max=73.67 min (pill significantly greater than gum, a=0.0075), and an average T-Max=73.67 min (pill significantly greater than gum, a=0.005). In other words, after ingesting a pill, it takes a longer amount of time to reach ½ of the peak plasma caffeine concentration and the peak plasma caffeine concentration than after chewing gum delivering the same level of caffeine.

3. The Abs. Rate Const. (absorption rate constant, rate at which caffeine absorbs into the bloodstream) was significantly greater for 50 mg pellet gum (Example 235) than for the 50 mg pill, indicating that caffeine is absorbed at a greater rate after gum delivery than after delivery of the same dosage via a pill. For the 50 mg pellet gum, the average Abs. Rate Const.=0.060 compared to the 50 mg pill with an average Abs. Rate Const.=0.031 (gum significantly greater than pill, a=0.005).

4. The test also demonstrated faster uptake of plasma caffeine via Example 236, 40 mg pellet gum, delivery during the early time intervals post dose 10 minutes to 30 minutes (T10–T30) when compared to 50 mg of caffeine delivered via a pill. Significance levels ranged from a=0.05 to a=0.20. For example, the average level of plasma caffeine (at T=10 minutes) present after 40 mg pellet gum is chewed is 0.228 μg/ml compared to 0.034 μg/ml for pill (difference was slightly significant, a=0.2). In other words, with caffeine being delivered from the two different vehicles at T10 there is 6.7 times more caffeine detected in plasma after chewing Example 236 gum caffeine than after ingesting a pill, even though the pill delivered approximately 50 mg caffeine, and Example 236 delivered approximately 40 mg. At T5, on average there was 13 times more caffeine detected in plasma after chewing Example 236 gum than after ingesting a pill.

5. Classical pharmacokinetic parameters, T-Max and Abs. ½ Life were significantly different for caffeine delivered via Example 236 40 mg pellet gum than via a 50 mg pill. Faster uptake of plasma caffeine was demonstrated via delivery from Example 236 gum compared to a pill due to the average plasma Abs. ½ Life and average plasma T-Max being significantly smaller for gum-than the pill. For the 50 mg Example 235 gum, the average Abs. ½ Life=18.33 min and the average T-Max=45 min compared to the 50 mg pill with an average Abs. ½ Life=24.47 min (pill significantly greater than gum, a=0.05), and an average T-Max=73.67 min (pill significantly greater than gum, a=0.15). Even though the Example 236 delivered 40 mg caffeine compared to delivery of 50 mg via a pill, it still took a longer amount of time to reach ½ of the peak plasma caffeine concentration the peak plasma caffeine concentration for the pill than for the gum.

6. It was concluded that gums formulated with all the caffeine in the pellet coating delivered caffeine more quickly to the plasma than gums formulated with the caffeine split between the coating and the center based upon the following:

Classical pharmacokinetic parameters T-Max and Abs. ½ Life were greater than pill for both 50 mg pellet and Example 235, though the level of significant difference was much greater for the 50 mg pellet (Example 235) (a=0.0075 and a=0.005 respectively) than Example 236 (a=0.05, a=0.15). The Abs. Rate Const. was significantly lower for the pill than for either the 50 mg pellet or the Example 236. Again, the level of significant difference was greater for the 50 mg pellet (Example 235), a=0.005 compared to 0.20 for Example 236.

7. Combining the conclusions from the two completed caffeine studies, it appears that rate of caffeine uptake in plasma via the various delivery vehicles tested follow this pattern:

Pellet with caffeine all in coating>Pellet with caffeine split between coating and center≈Beverages coffee/cola>Pill Caffeine was chosen as a model for drug delivery tests because it is a food approved, pharmacologically active agent that is readily detected in plasma at a wide range of dosage levels. It is widely consumed via a number of delivery vehicles, including liquids (coffee, cola, and pills). Drugs are administered through different delivery vehicles, two oral delivery vehicles being liquid syrups and pills. Testing caffeinated beverages and pills vs. caffeinated gums should give an indication of how similar drugs administered as liquids or coated pills vs. coated gum could behave.

It should be appreciated that the compositions and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention, therefore, indicated by the appended claims rather than by the foregoing description. All changes which come within the meaning and range of equivalency of the claims are to be embraced within their scope.

What is claimed is:

1. A method of producing coated chewing gum products containing at least one active agent in the coating so as to modify the release of the active agent in the mouth comprising the steps of:
   a) providing chewing gum product cores;
   b) providing a coating solution containing a bulk sweetener;
   c) providing a powder material comprising an active agent; and
   d) coating the chewing gum product cores with the coating solution and powder material, with the powder material being applied as a dry charge between two or more applications of the coating solution, to provide coated chewing gum products, the coating including the active agent, and the active agent being present at a level of from about 2% to about 5% in the gum products.

2. The method of claim 1 wherein the active agent is present in the coating at a level of from about 0.01% to about 2.5% of the coating.

3. The method of claim 1 wherein a high-potency sweetener selected from the group consisting of aspartame, alitame, salts of acesulfame, cyclamate and its salts, saccharine and its salts, neotame, thaumatin, monellin, dihydrochalcones, sucralose and combinations thereof is mixed in the coating solution.

4. The method of claim 1 wherein said active agent is selected from the group consisting of vitamins, analgesics, antacids, antihistamines, antitussives, antibacterial agents, decongestants and anesthetics.

5. The method of claim 1 wherein said active agent is selected from the group consisting of asprin, acetaminophen, ketoprofen, naproxen, and ibuprofen.

6. The method of claim 1 wherein said active agent is an antacid selected from the group consisting of cimetidine, rantidine, omeprazole and famotidine.

7. The method of claim 1 wherein said active agent is an antihistamine selected form the group consisting of cimetidine, rantidine, famotidine and chlorpheniramine maleate.

8. The method of claim 1 wherein said active agent is selected from the group consisting of dextromethorphan hydrobromide and pseudoephedrine hydrochloride.

9. The method of claim 1 wherein the active agent is a nutraceutical.

10. The method of claim 1 wherein said active agent is selected from the group consisting of nicotine and nicotine substitutes.

11. The method of claim 1 wherein active agent is included in both the coating solution and the powder material.

12. The method of claim 1 wherein an active agent is also included in the chewing gum cores.

13. The method of claim 12 wherein the active agents in the gum cores and coating are the same;

14. The method of claim 12 wherein the active agent in the gum cores is different than the active agent in the coating.

* * * * *

UNITED STATES PATENT AND TRADEMARK OFFICE
CERTIFICATE OF CORRECTION

PATENT NO. : 6,627,234 B1
DATED : September 30, 2003
INVENTOR(S) : Sonya S. Johnson et al.

It is certified that error appears in the above-identified patent and that said Letters Patent is hereby corrected as shown below:

Title page,
Item [62], Related U.S. Application Data, delete "Continuation", and substitute -- This application claims benefit of 60/112,389, filed on Dec. 15, 1998 and a continuation --
Item [56], References Cited, U.S. PATENT DOCUMENTS, delete "Fuysz" reference "Fuysz" reference, delete "Fuysz"and substitute -- Fuisz --
"Huzoinec et al." reference, delete "Huzoinec et al." and substitute -- Huzinec et al. --
"Gumtech International, Inc." reference, delete "package "Chem &" and substitute -- package "Chew & --
"Akitoshi" reference, delete "112:126228t," and substitute -- 112:125228t, --
"Warren et al." reference, after (1992) delete "*Cance*" and substitute -- *Cancer* --

Column 46,
Line 11, after "from about" delete "2%" and substitute -- 0.2% --
Line 59, immediately after "are the same" delete ";" (semicolon) and substitute -- . -- (period)

Signed and Sealed this

Twelfth Day of October, 2004

JON W. DUDAS
*Director of the United States Patent and Trademark Office*